US010377990B2

(12) United States Patent
Lin et al.

(10) Patent No.: US 10,377,990 B2
(45) Date of Patent: Aug. 13, 2019

(54) VIRAL RESISTANT CELLS AND USES THEREOF

(71) Applicant: SIGMA-ALDRICH CO. LLC, St. Louis, MO (US)

(72) Inventors: Nan Lin, St. Louis, MO (US); Joaquina Mascarenhas, St. Louis, MO (US); Audrey Chang, St. Louis, MO (US); David Onions, St. Louis, MO (US); Henry George, St. Louis, MO (US); Kevin Kayser, St. Louis, MO (US)

(73) Assignee: SIgma-Aldrich Co. LLC, St. Louis, MO (US)

( * ) Notice: Subject to any disclaimer, the term of this patent is extended or adjusted under 35 U.S.C. 154(b) by 0 days.

(21) Appl. No.: 15/122,311

(22) PCT Filed: Mar. 3, 2015

(86) PCT No.: PCT/US2015/018474
§ 371 (c)(1),
(2) Date: Aug. 29, 2016

(87) PCT Pub. No.: WO2015/134488
PCT Pub. Date: Sep. 11, 2015

(65) Prior Publication Data
US 2016/0369240 A1 Dec. 22, 2016

Related U.S. Application Data

(60) Provisional application No. 61/947,860, filed on Mar. 4, 2014.

(51) Int. Cl.
C12N 5/00 (2006.01)
C12N 5/071 (2010.01)
C12N 9/10 (2006.01)

(52) U.S. Cl.
CPC ............ C12N 5/0682 (2013.01); C12N 5/00 (2013.01); C12N 9/1051 (2013.01); C12Y 204/01101 (2013.01); C12Y 204/01144 (2013.01); C12Y 204/01155 (2013.01); C12N 2501/724 (2013.01); C12N 2510/02 (2013.01); C12N 2720/12011 (2013.01); C12N 2750/14311 (2013.01)

(58) Field of Classification Search
None
See application file for complete search history.

(56) References Cited

U.S. PATENT DOCUMENTS

| | | | |
|---|---|---|---|
| 2011/0016546 A1 | 1/2011 | Bedell et al. | |
| 2011/0030072 A1* | 2/2011 | Weinstein | A01K 67/0275 800/3 |
| 2013/0039991 A1 | 2/2013 | Varki et al. | |
| 2013/0164329 A1* | 6/2013 | Rossomando | A61K 39/15 424/215.1 |
| 2013/0243744 A1* | 9/2013 | Betenbaugh | C12Y 204/01214 424/94.3 |
| 2014/0099666 A1* | 4/2014 | Rossomando | C12N 15/111 435/68.1 |

FOREIGN PATENT DOCUMENTS

WO 2015/134488 A1 9/2015

OTHER PUBLICATIONS

Kajigaya et al in "A genetically engineered cell line that produces empty capsids of B19 (human) parvovirus" (Proc Natl Acad Sci Oct. 1989, vol. 86, No. 19, pp. 7601-7605).*
Fan et al "Improving the efficiency of CHO cell line generation using glutamine synthetase gene knockout cells" (Biotechnol Bioeng Apr. 2012 vol. 109, No. 4, pp. 1007-1015; published online Nov. 21, 2011).*
Chen et al in "Five Lec1 CHO cell mutants have distinct Mgat1 gene mutations that encode truncated N-acetylglucosaminyltransferase 1"(Glycobiology vol. 13, No. 1, pp. 43-50, 2003). (Year: 2003).*
Ball-Goodrich et al., "Two Amino Acid Substitutions within the Capsid Are Coordinately Required for Acquisition of Fibrotropism by the Lymphotropic Strain of Minute Virus of Mice", Journal of Virology, 1992, pp. 3415-3423, vol. 66, No. 6.
Becker et al., "Serological survey of virus infection among wild house mice (*Mus domesticus*) in the UK", Laboratory Animals, 2007, pp. 229-238, vol. 41.
Besselsen et al., "Molecular characterization of newly recognized rodent parvoviruses", Journal of General Virology, 1996, pp. 899-911, vol. 77.
D'Abramo Jr. et al., "Host range mutants of Minute Virus of Mice with a single VP2 amino acid change require additional silent mutations that regular NS2 accumulation", Virology, 2005, pp. 143-154, vol. 340.
Etingov et al., "An extension of the Minute Virus of Mice tissue tropism", Virology, 2008, pp. 245-255, vol. 379.
Gardiner et al., "Mapping of the Fibrotropic and Lymphotropic Host Range Determinants of the Parvovirus Minute Virus of Mice", Journal of Virology, 1988, pp. 2605-2613, vol. 62, No. 8.
Garnick, "Raw Materials as a Source of Contamination in Large-Scale Cell Culture", Dev Biol. Stand., 1998, pp. 21-29, vol. 93.
Halder et al., "Profiling of Glycan Receptors for Minute Virus of Mice in Permissive Cell Lines Towards Understanding the Mechanism of Cell Recognition", PLoS ONE, 2014, e86909, 12 pgs., vol. 9, No. 1.
International Search Report and Written Opinion from related International Application No. PCT/US2015/018474, dated May 26, 2015, 11 pgs.

(Continued)

Primary Examiner — Catherine S Hibbert
(74) Attorney, Agent, or Firm — Daniel S. Kasten

(57) ABSTRACT

The present invention provides mammalian cell lines that have been genetically engineered causing such cell lines to be resistant to viral entry and/or propagation, and provides methods of using said cell lines to reduce or prevent viral contamination of biologic production systems.

11 Claims, 7 Drawing Sheets
Specification includes a Sequence Listing.

(56) References Cited

OTHER PUBLICATIONS

Kiss, "Practicing Safe Cell Culture: Applied Process Designs for Minimizing Virus Contamination Risk", PDA Journal of Pharmaceutical Science and Technology, 2011, pp. 715-729, vol. 65, No. 6.

Kontou et al., "Structural Determinants of Tissue Tropism and In Vivo Pathogenicity for the Parvovirus Minute Virus of Mice", Journal of Virology, 2005, pp. 10931-10943, vol. 79, No. 17.

Lagna et al., "Use of Dominant Negative Constructs to Modulate Gene Expression", Current Topics in Developmental Biology, 1998, pp. 75-98, vol. 36.

Lee et al., "Site-specific integration in CHO cells mediated by CRISPR/Cas9 and homology-directed DNA repair pathway", Scientific Reports, 2015, pp. 1-11, vol. 5.

Lim et al., "The Golgi CMP-sialic acid transporter: A new CHO mutant provides functional insights", Glycobiology, 2008, pp. 851-860, vol. 18, No. 11.

Madsen et al., "Glycan Elongation Beyond the Mucin Associated Tn Antigen Protects Tumor Cells from Immune-Mediated Killing", PLoS ONE, 2013, e72413, pp. 1-11, vol. 8, No. 9.

Matrosovich et al., "Sialic Acid Receptors of Viruses", Top Curr Chem, 2015, pp. 1-28, vol. 367.

Maxwell et al., "The Capsid Determinant of Fibrotropism for the MVMp Strain of Minute Virus of Mice Functions via VP2 and Not VP1", Journal of Virology, 1995, pp. 5829-5832, vol. 69, No. 9.

Nam et al., "Identification of the Sialic Acid Structures Recognized by Minute Virus of Mice and the Role of Binding Affinity in Virulence Adaptation", Journal of Biological Chemistry, 2006, pp. 25670-25677, vol. 281, No. 35.

Nettleton et al., "The Association of Calf Serum with the Contamination of BHK21 Clone 13 Suspension Cells by a Parvovirus Serologically Related to the Minute Virus of Mice (MVM)", Archives of Virology, 1980, pp. 359-374, vol. 64.

Onions, "Animal Virus Contaminants of Biotechnology Products", Dev Biol. (Basel), 2004, pp. 155-163, vol. 118.

Ronda et al., "Accelerating Genome Editing in CHO Cells Using CRISPR Cas9 and CRISPy, a Web-Based Target Finding Tool", Biotechnology and Bioengineering, 2014, pp. 1604-1616, vol. 111, No. 8.

Rubio et al., "Genome Replication and Postencapsidation Functions Mapping to the Nonstructural Gene Restrict the Host Range of a Murine Parvovirus in Human Cells", Journal of Virology, 2001, pp. 11573-11582, vol. 75, No. 23.

Rubio et al., "Virulent Variants Emerging in Mice Infected with the Apathogenic Prototype Strain of the Parvovirus Minute Virus of Mice Exhibit a Capsid with Low Avidity for a Primary Receptor", Journal of Virology, 2005, pp. 11280-11290, vol. 79, No. 17.

Tattersall et al., "Reciprocal Productive and Restrictive Virus-Cell Interactions of Immunosuppressive and Prototype Strains of Minute Virus of Mice", Journal of Virology, 1983, pp. 944-955, vol. 46, No. 3.

Ventoso et al., "Translation Control by Protein Kinase R Restricts Minute Virus of Mice Infection: Role in Parvovirus Oncolysis", Journal of Virology, 2010, pp. 5043-5051, vol. 84, No. 10.

Yang, "Applications of a Novel CHO Glycosylation Mutant", Doctoral Dissertation, University of Singapore, Jan. 2014; 127 pgs.

Zoletto, "Parvovirus Serologically Related to the Minute Virus of Mice (MVM) as Contaminant of BHK 21 CL. 13 Suspension Cells", Dev Biol. Stand., 1985, pp. 179-183, vol. 60.

\* cited by examiner

SEQUENCE LISTING

```
<160> NUMBER OF SEQ ID NOS: 18

<210> SEQ ID NO 1
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 1

Pro Lys Lys Lys Arg Lys Val
1               5

<210> SEQ ID NO 2
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 2

Pro Lys Lys Lys Arg Arg Val
1               5

<210> SEQ ID NO 3
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 3

Lys Arg Pro Ala Ala Thr Lys Lys Ala Gly Gln Ala Lys Lys Lys Lys
1               5                   10                  15

<210> SEQ ID NO 4
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 4

Gly Arg Lys Lys Arg Arg Gln Arg Arg Arg Pro Pro Gln Pro Lys Lys
1               5                   10                  15

Lys Arg Lys Val
            20

<210> SEQ ID NO 5
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 5

Pro Leu Ser Ser Ile Phe Ser Arg Ile Gly Asp Pro Pro Lys Lys Lys
1               5                   10                  15

Arg Lys Val
```

<210> SEQ ID NO 6
<211> LENGTH: 24
<212> TYPE: PRT
<213> ORGANISM: Artificial Sequence
<220> FEATURE:
<223> OTHER INFORMATION: SYNTHESIZED

<400> SEQUENCE: 6

Gly Ala Leu Phe Leu Gly Trp Leu Gly Ala Ala Gly Ser Thr Met Gly
1               5                   10                  15

Ala Pro Lys Lys Lys Arg Lys Val
            20

<210> SEQ ID NO 7
<211> LENGTH: 27
<212> TYPE: PRT
<213> ORGANISM: Artificial Sequence
<220> FEATURE:
<223> OTHER INFORMATION: SYNTHESIZED

<400> SEQUENCE: 7

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 8
<211> LENGTH: 21
<212> TYPE: PRT
<213> ORGANISM: Artificial Sequence
<220> FEATURE:
<223> OTHER INFORMATION: SYNTHESIZED

<400> SEQUENCE: 8

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 9
<211> LENGTH: 39
<212> TYPE: DNA
<213> ORGANISM: Cricetulus griseus

<400> SEQUENCE: 9
aacaagttca agttcccagc agctgtggta gtggaggac                              39

<210> SEQ ID NO 10
<211> LENGTH: 43
<212> TYPE: DNA
<213> ORGANISM: Cricetulus griseus

<400> SEQUENCE: 10
gccttctcag tgttccggaa aagtgtcctg aacaaggtgg gat                         43

<210> SEQ ID NO 11
<211> LENGTH: 39
<212> TYPE: DNA
<213> ORGANISM: Cricetulus griseus

<400> SEQUENCE: 11
ttcctggacc acttcccacc cggtggccgg caggatggc                              39

```
<210> SEQ ID NO 12
<211> LENGTH: 45
<212> TYPE: DNA
<213> ORGANISM: Cricetulus griseus

<400> SEQUENCE: 12
ttctgcactt caccatccag cagcggactc agcctgagag cagct            45

<210> SEQ ID NO 13
<211> LENGTH: 43
<212> TYPE: DNA
<213> ORGANISM: Cricetulus griseus

<400> SEQUENCE: 13
agcttatacc gtagctttaa gatacacaag gacaacagct aaa              43

<210> SEQ ID NO 14
<211> LENGTH: 43
<212> TYPE: DNA
<213> ORGANISM: Cricetulus griseus

<400> SEQUENCE: 14
ggcagcctcc agtgtcgtcg ttgtgttgtg gtggggaatg ggc              43

<210> SEQ ID NO 15
<211> LENGTH: 39
<212> TYPE: DNA
<213> ORGANISM: Cricetulus griseus

<400> SEQUENCE: 15
cggtacctct gattttgctt tgccctatgg gacaaggcc                   39

<210> SEQ ID NO 16
<211> LENGTH: 39
<212> TYPE: DNA
<213> ORGANISM: Cricetulus griseus

<400> SEQUENCE: 16
accctcatgc tagacattta gatgataacg aacccagtc                   39

<210> SEQ ID NO 17
<211> LENGTH: 39
<212> TYPE: DNA
<213> ORGANISM: Cricetulus griseus

<400> SEQUENCE: 17
ttcaagctat actgcttggc agtgatgact ctggtggct                   39

<210> SEQ ID NO 18
<211> LENGTH: 13
<212> TYPE: DNA
<213> ORGANISM: Artificial Sequence
<220> FEATURE:
<223> OTHER INFORMATION: SYNTHESIZED

<400> SEQUENCE: 18
gccgccacca atg                                               13
```

US 10,377,990 B2

VIRAL RESISTANT CELLS AND USES THEREOF

CROSS-REFERENCE TO RELATED APPLICATIONS

This application is a U.S. National Stage Application of PCT International Application No. PCT/US2015/018474, filed Mar. 3, 2015, which claims priority to U.S. Provisional Application Ser. No. 61/947,860, filed Mar. 4, 2014, the disclosure of each is hereby incorporated by reference in its entirety.

FIELD OF THE INVENTION

The present disclosure relates to mammalian cell lines engineered to have viral resistance and the use of said cell lines to reduce or prevent viral contamination of biologic production systems.

BACKGROUND

The use of recombinantly-produced therapeutic proteins for the treatment of many diseases or conditions such as cancer and autoimmune diseases continues to increase. However, large-scale production of these protein therapeutics still remains a challenge. For example, the commercial manufacturing process must deliver a reliably high-yield with downstream processes producing an extremely pure product allowing only trace amounts, to preferably, no contaminants.

The use of animal component-free media has significantly reduced the incidence of adventitious viral contamination. Additionally, the implementation of procedures such as ultrafiltration, high temperature short time processing, and/or UVC irradiation of bulk materials has further reduced the incidence of contamination. Nevertheless, the risk of viral contamination still remains. A contamination incident would be catastrophic for the manufacturer in terms of loss of product, temporary withdrawal for the market, and extensive decontamination costs. Thus, there is a need for mammalian cell lines having increased resistance to viral infection.

SUMMARY

Figure 1:
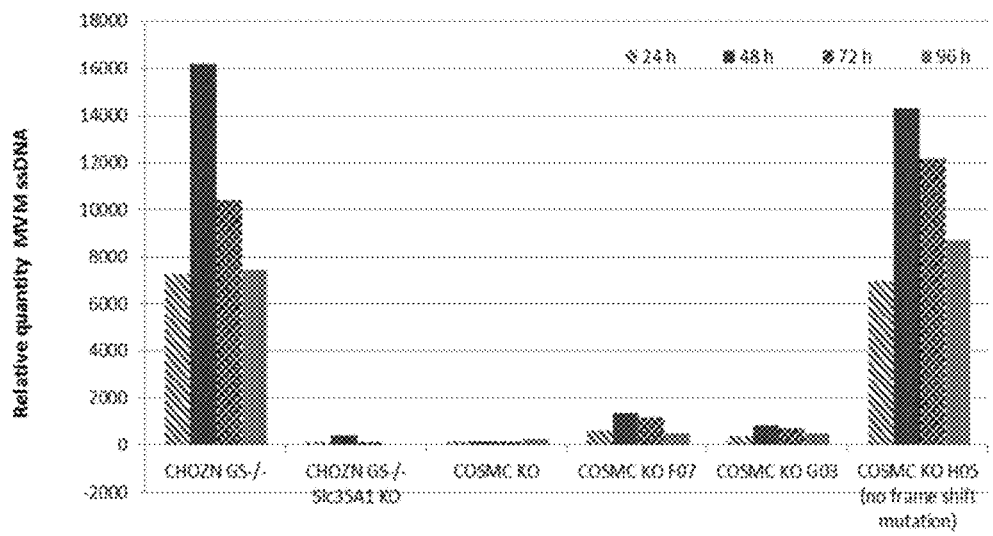
FIG. 1 presents a time course of MVM viral infection as assayed by Southern blot analysis. Plotted with the relative quantity of MVM viral DNA detected at 24, 48, 72 and 96 hours for wild-type cells (CHOZN GS−/−), Slc35A1 KO, COSMC KO, COSMC KO clone F07, COSMC KO clone G03, and COSMC KO clone H05. Clone H05 has an in-frame deletion of 12 bp (i.e., a no frame shift mutation).

Among the various aspects of the present disclosure is the provision of mammalian cell lines that are engineered to hinder or prevent viral entry and/or viral propagation in the cells. In some embodiments, the mammalian cell lines are genetically modified such that entry and/or propagation of at least one virus is reduced or eliminated as compared to unmodified parental cell lines. In various embodiments, the mammalian cell lines disclosed herein comprise at least one modified chromosomal sequence. In further embodiments, the modified chromosomal sequence is inactivated such that the cell line produces no or reduced levels of the encoded protein product.

In one embodiment, the cell line comprises at least one inactivated chromosomal sequence encoding Core 1 enzyme chaperone (COSMC). In another embodiment, all copies of chromosomal sequences encoding COSMC are inactivated and the cell line produces no COSMC. In an alternate embodiment, the cell line comprises at least one inactivated chromosomal sequence encoding solute carrier family 35 (CMP-sialic acid transporter) member A1 (Slc35A1). In another embodiment, all copies of chromosomal sequences encoding Slc35A1 are inactivated and the cell line produces no Slc35A1. In still another embodiment, the cell line comprises at least one inactivated chromosomal sequence encoding core 1 elongation enzyme (C1GalT1). In a further embodiment, all copies of chromosomal sequences encoding C1GalT1 are inactivated and the cell line produces no C1GalT1. In a further embodiment, the cell line comprises at least one inactivated chromosomal sequence encoding St3 beta-galactoside alpha-2,3-sialyltransferase 1 (St3Gal1). In another embodiment, all copies of chromosomal sequences encoding St3Gal1 are inactivated and the cell line produces no St3Gal1. In an alternate embodiment, the cell line comprises at least one inactivated chromosomal sequence encoding St3 beta-galactoside alpha-2,3-sialyltransferase 2 (St3Gal2). In another embodiment, all copies of chromosomal sequences encoding St3Gal2 are inactivated and the cell line produces no St3Gal2. In yet another embodiment, the cell line comprises at least one inactivated chromosomal sequence encoding St3 beta-galactoside alpha-2,3-sialyltransferase 3 (St3Gal3). In a further embodiment, all copies of chromosomal sequences encoding St3Gal3 are inactivated and the cell line produces no St3Gal3. In still another embodiment, the cell line comprises at least one inactivated chromosomal sequence encoding St3 beta-galactoside alpha-2,3-sialyltransferase 4 (St3Gal4). In another embodiment, all copies of chromosomal sequences encoding St3Gal4 are inactivated and the cell line produces no St3Gal4. In an alternate embodiment, the cell line comprises at least one inactivated chromosomal sequence encoding St3 beta-galactoside alpha-2,3-sialyltransferase 5 (St3Gal5). In a further embodiment, all copies of chromosomal sequences encoding St3Gal5 are inactivated and the cell line produces no St3Gal5. In yet another embodiment, the cell line comprises at least one inactivated chromosomal sequence encoding St3 beta-galactoside alpha-2,3-sialyltransferase 6 (St3Gal6). In a further embodiment, all copies of chromosomal sequences encoding St3Gal6 are inactivated and the cell line produces no St3Gal6. In an alternate embodiment, the cell line comprises inactivated chromosomal sequences encoding any two of St3Gal1, St3Gal2, St3Gal3, St3Gal4, St3Gal5, and St3Gal6. In yet another embodiment, the cell line comprises inactivated chromosomal sequences encoding any three of St3Gal1, St3Gal2, St3Gal3, St3Gal4, St3Gal5, and St3Gal6. In further embodiments, cell lines comprising inactivated chromosomal sequences encoding COSMC, Slc35A1, C1GalT1, St3Gal1, St3Gal2, St3Gal3, St3Gal4, St3Gal5, and/or St3Gal6 further comprise inactivated chromosomal sequences encoding mannosyl (alpha-1,3-)-glycoprotein beta-1,2-N-acetylglucosaminyltransferase 1 (Mgat1), mannosyl (alpha-1,6-)-glycoprotein beta-1,2-N-acetylglucosaminyltransferase 2 (Mgat2), mannosyl (alpha-1,4-)-glycoprotein beta-1,4-N-acetylglucosaminyltransferase 3 (Mgat3), mannosyl (alpha-1,3-)-glycoprotein beta-1,4-N-acetylglucosaminyltransferase 4 (Mgat4), and/or mannosyl (alpha-1,6-)-glycoprotein beta-1,6-N-acetylglucosaminyltransferase 5 (Mgat5). The mammalian cell lines disclosed herein comprising modified chromosomal sequence have increased resistance to viral entry and/or viral propagation as compared to the unmodified parental cell lines. In still other embodiments, cell lines comprising inactivated chromosomal sequences encoding St3Gal1, St3Gal2, St3Gal3, St3Gal4, St3Gal5, and/or St3Gal6 are further engineered to overexpress at least one sialyltransferase responsible for making 2,6-linkages (e.g., St6 beta-galactosamide alpha-2,6-sialyltranferase 1 (St6Gal1), St6 beta-galactosamide alpha-2,6-sialyltranferase 2 (St6Gal2), St6 (alpha-N-acetyl-neuraminyl-2,3-beta-galactosyl-1,3)-N-acetylgalactosaminide 1 (St6GalNac1), St6 (alpha-N-acetyl-neuraminyl-2,3-beta-galactosyl-1,3)-N-acetylgalactosaminide 2 (St6GalNac2), St6 (alpha-N-acetyl-neuraminyl-2,3-beta-galactosyl-1,3)-N-acetylgalactosaminide 3 (St6GalNac3), St6 (alpha-N-acetyl-neuraminyl-2,3-beta-galactosyl-1,3)-N-acetylgalactosaminide 4 (ST6GalNac4), St6 (alpha-N-acetyl-neuraminyl-2,3-beta-galactosyl-1,3)-N-acetylgalactosaminide 5 (St6GalNac5), and/or St6 (alpha-N-acetyl-neuraminyl-2,3-beta-galactosyl-1,3)-N-acetylgalactosaminide 6 (St6GalNac6).

In some embodiments, the mammalian cell lines are non-human cell lines. In other embodiments, the mammal cell lines are Chinese hamster ovary (CHO) cell lines. In specific embodiments, the cell line is a CHO cell line comprising inactivated chromosomal sequences encoding COSMC, Slc35A1, C1GalT1, St3Gal1, St3Gal2, St3Gal3, St3Gal4, St3Gal5, St3Gal6, or combinations thereof.

In certain embodiments, the mammalian cell lines disclosed herein exhibit resistance to entry and/or propagation of viruses chosen from parvovirus, reovirus, rotavirus, influenza virus, adeno-associated virus, calicivirus, parainfluenza virus, rubella virus, coronavirus, norovirus, encephalomyocarditis virus, polyomavirus, or combinations thereof. In some embodiments, the parovirus is minute virus of mouse (MVM), mouse parvovirus type-1, mouse parvovirus type-2, mouse parvovirus type-3, porcine parvovirus 1, bovine parovirus 1, human parovirus B19, human parovirus 4, human parovirus 5, or combinations thereof. In additional embodiments, the reovirus is mammalian reovirus-3, mammalian orthoreovirus, avian orthoreovirus, or combinations thereof.

In various embodiments, the mammalian cell lines disclosed herein are prepared by modifying at least one chromosomal sequence using a targeting endonuclease-mediated genome modification technique. The targeting endonuclease can be zinc finger nucleases, CRISPR/Cas endonuclease, transcription activator-like effector (TALE) nuclease, meganuclease, a site-specific endonuclease, or an artificial targeted DNA double strand break inducing agent. In specific embodiments, the targeting endonuclease is a pair of zinc finger nucleases.

In some embodiments, the mammalian cell lines disclosed herein further comprising at least one nucleic acid encoding a recombinant protein chosen from an antibody, an antibody fragment, a vaccine, a growth factor, a cytokine, a hormone, a clotting factor, or another therapeutic protein.

Another aspect of the present disclosure encompasses a method for reducing or preventing viral contamination of a recombinant protein product, the method comprising obtaining a viral resistant mammalian cell line as disclosed herein and expressing the recombinant protein product in the cell line.

A further aspect of the present disclosure provides a method for reducing the risk of viral contamination of a biologic production system, wherein the method comprises providing a viral resistant mammalian cell line as disclosed herein for use in the biologic production system.

Still another aspect of the present disclosure encompasses a composition comprising a viral resistant mammalian cell line as disclosed herein and at least one virus, wherein the cell line exhibits resistance to infection by the at least one virus.

Other aspect and iterations of the disclosure are described in more detail below.

DETAILED DESCRIPTION

The present disclosure provides mammalian cell lines engineered to hinder or prevent viral entry and/or viral propagation in the cell lines. The engineered cell lines having viral resistance can be genetically modified to contain modified (e.g., inactivated) chromosomal sequences. Also provided are methods of using the cell lines disclosed herein for the production of recombinant proteins, wherein the recombinant protein products are essentially devoid of viral contamination. Use of the cell lines that are resistant to viral infection, therefore, reduces or eliminates the risk of viral contamination of biologic production systems and the resultant protein products.

(I) Viral Resistant Cell Lines

One aspect of the present disclosure encompasses mammalian cell lines that are engineered to have viral resistance. Stated another way, the cell lines disclosed herein have increased resistance to infection by at least one virus as compared to unmodified, parental cell lines. More specifically, entry of the virus and/or propagation of the virus is reduced or eliminated in the engineered cell lines disclosed herein as compared to unmodified parental cell lines. In some embodiments, the mammalian cell lines are genetically modified and contain at least one modified chromosomal sequence. In general, the modified sequence comprises a mutation. In specific embodiments, the modified chromosomal sequence is inactivated (or knocked out) such that the encoded protein product is not produced by the cell line.

In general, resistance (or susceptibility) to viral infection can be determined by comparing the response of the engineered mammalian cell lines to exposure to a virus or viruses with the response of unmodified (non-engineered) parental cells to the same viral challenge. Viral infection of the cell line and/or viral propagation in the cell line can be analyzed by a variety of techniques. Non-limiting examples of suitable techniques include nucleic acid detection methods (e.g., Southern nucleic acid blotting assay to detect the presence of specific viral nucleic acids, PCR or RT-PCR to detect viral nucleic acids, sequencing methods, and the like), antibody-based techniques (e.g., Western immunoblotting techniques using anti-viral protein antibodies, ELISA methods, and so forth), bioassays, (e.g., plaque assays, cytopathic effect assays, and the like), and microscopic techniques (e.g., electron microscopy to detect viral particles, etc.). In some embodiments, infection and/or propagation of the virus within the engineered mammalian cell lines can be reduced by at least about 10%, at least about 20%, at least about 40%, at least about 60%, at least about 80%, at least about 90%, at least about 99%, or more than about 99% relative to that of unmodified parental cells. In specific embodiments, the engineered mammalian cell lines are resistant to viral infection, i.e., the virus is unable to enter and/or propagate in the engineered mammalian cell lines.

The mammalian cell lines disclosed herein can be engineered in a variety of different ways to impart viral resistance. In some embodiments, the cell lines can be modified such that viral entry via cell surface receptors is reduced or eliminated. In other embodiments, the cell lines can be engineered to express molecules that inhibit or block specific viral proteins involved in replication and/or infectivity. In still other embodiments, the cell lines can be engineered to overexpress specific cellular antiviral proteins. In some embodiments, the engineering can be genetic, wherein genomic or chromosomal sequences are modified. Stated another way, the cell lines are genetically modified. In other embodiments, the engineering can be epigenetic or extrachromosomal.

(a) Mechanism of Viral Resistance (i) Perturbation of Cell Surface Receptors

In certain embodiments, the mammalian cell lines are engineered to contain altered cell surface receptors. Viruses can enter cells via specific attachment to complementary receptors on the surface of cells. For many viruses, these cell surface receptors comprise glycan structures linked to proteins (or lipids). Glycans terminating in sialic acid or its derivatives serve as receptors for many viruses (Matrosovich et al., 2013, Top Curr Chem, DOI: 10.1007/128_2013_466). Thus, glycoproteins comprising O-linked or N-linked glycans with terminal sialic acid residues can function as cell surface receptors for numerous viruses. Sialic acid refers to derivatives of neuraminic acid, and includes, for example, N-acetylneuraminic acid (Neu5Ac or NANA) and N-glycolylneuraminic acid (Neu5Gc or NGNA).

In some embodiments, the cell lines are engineered to comprise glycoproteins lacking terminal sialic acid residues. Terminal sialic acid residues can be eliminated by deleting (i.e., knocking out) or altering enzymes and/or proteins involved in the synthesis of glycan chains. Suitable targets include enzymes or proteins involved in the synthesis of O-linked glycans, enzymes or proteins involved in the synthesis of N-linked glycans, and/or enzymes or proteins involved in the synthesis or transport of sialic acid.

In certain embodiments, the cell line can be deficient in at least one of the above-mentioned targeted enzymes or proteins (or any combination of the above-mentioned targets). As used herein, "deficient" refers to reduced or non-detectable levels of the targeted enzymes or proteins, or reduced or non-detectable activity of the targeted enzymes or proteins. The amount or activity of the targeted enzyme or protein can be reduced or eliminated by modifying at least one chromosomal sequence encoding the targeted protein or enzyme. For example, the chromosomal sequence can be modified to contain a deletion of at least one nucleotide, an insertion of at least one nucleotide, a substitution of at least one nucleotide, or a combination thereof. Accordingly, the deletion(s), insertion(s), and/or substitution(s) can shift the reading frame of the chromosomal sequence such that no protein product is produced (i.e., the chromosomal sequence is inactivated). Alternatively, the deletion(s), insertion(s), and/or substitution(s) in the modified chromosomal sequence can lead to the production of an altered protein product. Modification of the chromosomal sequences of interest can be accomplished using targeted endonuclease-mediated genomic editing techniques, which are detailed below in section (III)(a). In cases in which one chromosomal sequence encoding the targeted enzyme or protein is inactivated, the engineered cell line produces reduced levels of the targeted enzyme or protein. In other cases in which all copies of the chromosomal sequence(s) encoding the targeted enzyme or protein are inactivated, the engineered cell line produces no targeted enzyme or protein (i.e., the cell line is a knock out or KO). In still other embodiments, the level of the targeted enzyme or protein can be reduced or eliminated using RNA interference-mediated mechanisms, which are described below in section (III)(b).

In some embodiments, the level of the targeted enzyme or protein can be reduced by at least about 5%, from about 5 to 10%, from about 10 to 20%, from about 20 to 30%, from about 30 to 40%, from about 40 to 50%, from about 50 to 60%, from about 60 to 70%, from about 70 to 80%, from about 80 to 90%, or from about 90 to about 100%. In other embodiments, the level of the targeted enzyme or protein can be reduced to non-detectable levels using techniques standard in the field (e.g., Western immunoblotting assays, ELISA enzyme assays, and the like).

In some embodiments, the cell line can be deficient in enzymes or proteins involved in O-linked glycosylation. For example, the cell line can be deficient in core 1 elongation enzyme (also called core 1 synthase glycoprotein-N-acetylgalactosamine 3-beta-galactosyltransferase 1 or C1GalT1), core 1 enzyme chaperone (also called C1GalT1-specific chaperone or COSMC), or both. COSMC facilitates the folding, stability, and activity C1GalT1, which catalyzes the transfer of a galactose residue to the N-acetylgalactosamine (GalNAc) residue that is O-linked to a serine or threonine of a protein. In specific embodiments, the cell line is deficient in C1GalT1, COSMC, or both. The deficiency can be due to inactivated chromosomal sequences encoding C1GalT1 and/or COSMC such that reduced levels or no C1GalT1 and/or COSMC protein is made. In some cases, at least one chromosomal sequence encoding C1GalT1 and/or COSMC is inactivated. In other cases, all copies of the chromosomal sequences encoding C1GalT1 and/or COSMC are inactivated, such that the cell line is devoid of C1GalT1 protein and/or COSMC protein.

In other embodiments, the cell line can be deficient in at least one sialyltransferase (ST). The sialyltransferase can be a sialyltransferase that adds sialic acid to galactose in an alpha-2,3 linkage conformation, a sialyltransferase that adds sialic acid to galactose or N-acetylgalactosamine in an alpha-2,6 linkage conformation, or a sialyltransferase that adds sialic acid to other sialic acid units in an alpha-2,8 linkage conformation. Non-limiting examples of suitable sialyltransferases include with St3 beta-galactoside alpha-2,3-sialyltransferase 1 (St3Gal1), St3 beta-galactoside alpha-2,3-sialyltransferase 2 (St3Gal2), St3 beta-galactoside alpha-2,3-sialyltransferase 3 (St3Gal3), St3 beta-galactoside alpha-2,3-sialyltransferase 4 (St3Gal4), St3 beta-galactoside alpha-2,3-sialyltransferase 5 (St3Gal5), St3 beta-galactoside alpha-2,3-sialyltransferase 6 (St3Gal6), St6 beta-galactosamide alpha-2,6-sialyltranferase 1 (St6Gal1), St6 beta-galactosamide alpha-2,6-sialyltranferase 2 (St6Gal2), St6 (alpha-N-acetyl-neuraminyl-2,3-beta-galactosyl-1,3)-N-acetylgalactosaminide 1 (St6GalNac1), St6 (alpha-N-acetyl-neuraminyl-2,3-beta-galactosyl-1,3)-N-acetylgalactosaminide 2 (St6GalNac2), St6 (alpha-N-acetyl-neuraminyl-2,3-beta-galactosyl-1,3)-N-acetylgalactosaminide 3 (St6GalNac3), St6 (alpha-N-acetyl-neuraminyl-2,3-beta-galactosyl-1,3)-N-acetylgalactosaminide 4 (ST6GalNac4), St6 (alpha-N-acetyl-neuraminyl-2,3-beta-galactosyl-1,3)-N-acetylgalactosaminide 5 (St6GalNac5), St6 (alpha-N-acetyl-neuraminyl-2,3-beta-galactosyl-1,3)-N-acetylgalactosaminide 6 (St6GalNac6), St8 alpha-N-acetyl-neuraminide alpha-2,8-sialyltransferase 1 (St8Sia1), St8 alpha-N-acetyl-neuraminide alpha-2,8-sialyltransferase 2 (St8Sia2), St8 alpha-N-acetyl-neuraminide alpha-2,8-sialyltransferase 3 (St8Sia3), St8 alpha-N-acetyl-neuraminide alpha-2,8-sialyltransferase 4 (St8Sia4), St8 alpha-N-acetyl-neuraminide alpha-2,8-sialyltransferase 5 (St8Sia5), or St8 alpha-N-acetyl-neuraminide alpha-2,8-sialyltransferase 6 (St8Sia6).

In specific embodiments, the cell line can be deficient in at least one alpha-2,3-sialyltransferase (e.g., St3Gal1, St3Gal2, St3Gal3, St3Gal4, St3Gal5, and/or St3Gal6). The deficiency can be due to inactivated chromosomal sequences encoding the at least one alpha-2,3-sialyltransferase such that reduced levels or none of the at least one alpha-2,3-sialyltransferase is made. In some cases, at least one chromosomal sequence encoding the at least one alpha-2,3-sialyltransferase can be inactivated. In other cases, all copies of the chromosomal sequences encoding the at least one alpha-2,3-sialyltransferase can be inactivated, such that the cell line is devoid of the at least one alpha-2,3-sialyltransferase. Stated another way, the chromosomal sequences encoding St3Gal 1, 2, 3, 4, 5, and/or 6 can be knocked out.

In some instances in which the cell line comprises at least one inactivated chromosomal sequences encoding the at least one alpha-2,3-sialyltransferase (e.g., St3Gal1, St3Gal2, St3Gal3, St3Gal4, St3Gal5, and/or St3Gal6), the cell line can be further engineered to overexpress at least one sialyltransferase responsible for making 2,6-linkages (e.g., St6Gal 1, St6Gal 2, St6GalNac1, St6GalNac2, St6GalNac3, ST6GalNac4, St6GalNac5, and/or St6GalNac6). Accordingly, such cell lines can comprise glycoproteins having reduced numbers (or no) terminal 2,3-linked sialic acid residues and increased numbers of terminal 2,6-linked sialic acid residues.

In further embodiments, the cell line can be deficient in at least one enzyme or protein involved in sialic acid synthesis or transport. Examples of enzymes or proteins involved in sialic acid synthesis or transport include, without limit, glucosamine (UDP-N-acetyl)-2-epimerase/N-acetylmannosamine kinase (GNE), N-acetylneuraminic acid synthase (NANS), N-acetylneuraminic acid phosphatase (NANP), cytidine monophosphate N-acetylneuraminic acid synthetase (CMAS), and cytidine monophosphate N-acetylneuraminic acid hydroxylase (CMAH), solute carrier family 35 (CMP-sialic acid transporter), member A1 (Slc35A1). In certain embodiments, the cell line can be deficient in Slc35A1, which transports CMP-sialic acid into the Golgi. In some cases, at least one chromosomal sequence encoding Slc35A1 can be inactivated. In other cases, all copies of the chromosomal sequences encoding Slc35A1 can be inactivated, such that the cell is devoid of Slc35A1 protein.

In additional embodiments, the cell line can be deficient in at least one enzyme or protein involved in N-glycosylation. In some instances, the enzyme or protein involved in N-glycosylation can be an N-acetylglucosylaminyltransferase, which adds a GlcNAc residue to a beta-linked mannose residue of an N-linked glycan. Examples include mannosyl (alpha-1,3-)-glycoprotein beta-1,2-N-acetylglucosaminyltransferase 1 (Mgat-1), mannosyl (alpha-1,6-)-glycoprotein beta-1,2-N-acetylglucosaminyltransferase 2 (Mgat-2), mannosyl (alpha-1,4-)-glycoprotein beta-1,4-N-acetylglucosaminyltransferase 3 (Mgat-3), mannosyl (alpha-1,3-)-glycoprotein beta-1,4-N-acetylglucosaminyltransferase 4 (Mgat-4), and mannosyl (alpha-1,6-)-glycoprotein beta-1,6-N-acetylglucosaminyltransferase 5 (Mgat-5). In other instances, the enzyme or protein involved in N-glycosylation can be a galactosyltransferase, which adds a galactose residue in a beta 1,4 linkage to a GlcNAc residue of an N-linked glycan. The galactosyltransferase, can be UDP-Gal:BetaGlcNAc beta 1,4-galactosyltransferase, polypeptide 1 (B4GalT1), UDP-Gal:BetaGlcNAc beta 1,4-galactosyltransferase, polypeptide 2 (B4GalT2), UDP-Gal:BetaGlcNAc beta 1,4-galactosyltransferase, polypeptide 3 (B4GalT3), UDP-Gal:BetaGlcNAc beta 1,4-galactosyltransferase, polypeptide 4 (B4GalT4), UDP-Gal:BetaGlcNAc beta 1,4-galactosyltransferase, polypeptide 5 (B4GalT5), UDP-Gal:BetaGlcNAc beta 1,4-galactosyltransferase, polypeptide 6 (B4GalT6), or UDP-Gal:BetaGlcNAc beta 1,4-galactosyltransferase, polypeptide 7 (B4GalT7). In certain cases, the cell line can be deficient in at least one N-acetylglucoylaminyltransferase and/or galactosyltransferase. In some iterations, at least one chromosomal sequence encoding the at least one N-acetylglucoylaminyltransferase and/or galactosyltransferase can be inactivated. In other cases, all copies of the chromosomal sequences encoding the at least one N-acetylglucoylaminyltransferase and/or galactosyltransferase can be inactivated, such that the cell line is devoid of the at least one N-acetylglucoylaminyltransferase and/or galactosyltransferase.

(ii) Interference with Viral Proteins

In other embodiments, the mammalian cell lines can be engineered to express molecules that inhibit or block viral replication and/or infectivity. For example, the cell lines can be engineered to stably express at least one RNA interference (RNAi) agent against specific viral proteins that are involved in replication and/or infectivity. Non-limiting examples of suitable viral proteins include nonstructural proteins such as NS1 or NS2, and capsid proteins such as VP1 or VP2. RNAi agents bind to target transcripts and prevent protein expression by mediating cleavage of the transcript cleavage or disrupting translation of the transcript.

In some embodiments, the RNAi agent can be a short interfering RNA (siRNA). In general, a siRNA comprises a double-stranded RNA molecule that ranges from about 15 to about 29 nucleotides in length, or more generally from about 19 to about 23 nucleotides in length. In specific embodiments, the siRNA can be about 21 nucleotides in length. The siRNA can optionally further comprise one or two single-stranded overhangs, e.g., a 3' overhang on one or both ends. The siRNA can be formed from two RNA molecules that hybridize together or, alternatively, can be generated from a short hairpin RNA (shRNA) (see below). In some embodiments, the two strands of the siRNA can be completely complementary, such that no mismatches or bulges exist in the duplex formed between the two sequences. In other embodiments, the two strands of the siRNA can be substantially complementary, such that one or more mismatches and/or bulges exist in the duplex formed between the two sequences. In certain embodiments, one or both of the 5' ends of the siRNA can have a phosphate group, while in other embodiments one or both of the 5' ends can lack a phosphate group.

One strand of the siRNA, which is referred to as the "antisense strand" or "guide strand," includes a portion that hybridizes with the target transcript. In some embodiments, the antisense strand of the siRNA can be completely complementary to a region of the target transcript, i.e., it hybridizes to the target transcript without a single mismatch or bulge throughout the length of the siRNA. In other embodiments, the antisense strand can be substantially complementary to the target region, i.e., one or more mismatches and/or bulges can exist in the duplex formed by the antisense strand and the target transcript. Typically, siRNAs are targeted to exonic sequences of the target transcript. Those of skill in the art are familiar with programs, algorithms, and/or commercial services that design siRNAs for target transcripts.

In other embodiments, the RNAi agent can be a short hairpin RNA (shRNA). In general, a shRNA is an RNA molecule comprising at least two complementary portions that are hybridized or are capable of hybridizing to form a double-stranded structure sufficiently long to mediate RNA interference (as described above), and at least one single-stranded portion that forms a loop connecting the regions of the shRNA that form the duplex. The structure can also be called a stem-loop structure, with the stem being the duplex portion. In some embodiments, the duplex portion of the structure can be completely complementary, such that no mismatches or bulges exist in the duplex region of the shRNA. In other embodiments, the duplex portion of the structure can be substantially complementary, such that one or more mismatches and/or bulges can exist in the duplex portion of the shRNA. The loop of the structure can be from about 1 to about 20 nucleotides in length, specifically from about 6 to about 9 nucleotides in length. The loop can be located at either the 5' or 3' end of the region that is complementary to the target transcript (i.e., the antisense portion of the shRNA).

The shRNA can further comprise an overhang on the 5' or 3' end. The optional overhang can be from about 1 to about 20 nucleotides in length, or more specifically from about 2 to about 15 nucleotides in length. In some embodiments, the overhang can comprise one or more U residues, e.g., between about 1 and about 5 U residues. In some embodiments, the 5' end of the shRNA can have a phosphate group. In general, shRNAs are processed into siRNAs by the conserved cellular RNAi machinery. Thus, shRNAs are precursors of siRNAs and are similarly capable of inhibiting expression of a target transcript that is complementary of a portion of the shRNA (i.e., the antisense portion of the shRNA). Those of skill in the art are familiar with the available resources for the design and synthesis of shRNAs. An exemplary example is MISSION® shRNAs (Sigma-Aldrich).

The siRNA or shRNA can be expressed in vivo from an RNAi expression construct. Suitable constructs include plasmid vectors, phagemids, cosmids, artificial/mini-chromosomes, transposons, and viral vectors (e.g., lentiviral vectors, adeno-associated viral vectors, etc.). In one embodiment, the RNAi expression construct can be a plasmid vector (e.g., pUC, pBR322, pET, pBluescript, and variants thereof). The RNAi expression construct can comprise two promoter control sequences, wherein each is operably linked appropriate coding sequence such that two separate, complementary siRNA strands can be transcribed. The two promoter control sequences can be in the same orientation or in opposite orientations. In another embodiment, the RNAi expression vector can contain a promoter control sequence that drives transcription of a single RNA molecule comprising two complementary regions, such that the transcript forms a shRNA. In general, the promoter control sequence(s) will be RNA polymerase III (Pol III) promoters such as U6 or H1 promoters. In other embodiments, RNA polymerase II (Pol II) promoter control sequences can be used (some examples are presented below). The RNAi expression constructs can contain additional sequence elements, such as transcription termination sequences, selectable marker sequences, etc. The RNAi expression construct can be introduced into the cell line of interest using standard procedures. The RNAi expression construct can be chromosomally integrated in the cell line for stable expression. Alternatively, the RNAi expression construct can be extrachromosomal (e.g., episomal) in the cell line for stable expression.

In still other embodiments, the cell lines can be engineered to stably express dominant negative forms of viral proteins involved in replication and/or infectivity. A dominant negative form of a protein is altered or mutated such that it out competes or inhibits the wild type protein. Non-limiting examples of suitable proteins include viral nonstructural proteins such as NS1 or NS2, and viral capsid proteins such as VP1 or VP2. In specific embodiments, the cell line can be engineered to express a dominant negative form of one or more NS1 proteins.

A dominant negative protein can have a deletion, an insertion, and/or a substitution relative to the wild type protein (Lagna et al., 1998, Curr. Topics Dev. Biol, 36:75-98). The deletion, insertion, and/or substitution can be at the N-terminal, C-terminal, or an internal location in the protein. Means for generating mutant proteins (via site-directed mutagenesis, PCR-based mutagenesis, random mutagenesis, etc.) are well known in the art, as are means for identifying those having dominant negative effects. Cell lines can be transfected with expression construct(s) (see above) comprising sequence encoding the dominant negative protein(s), wherein the coding sequence is operably linked to a Pol II promoter control sequence for expression. The promoter control sequence can be constitutive, regulated, or tissue-specific.

Suitable constitutive promoter control sequences include, but are not limited to, cytomegalovirus immediate early promoter (CMV), simian virus (SV40) promoter, adenovirus major late promoter, Rous sarcoma virus (RSV) promoter, mouse mammary tumor virus (MMTV) promoter, phosphoglycerate kinase (PGK) promoter, elongation factor (ED1)-alpha promoter, ubiquitin promoters, actin promoters, tubulin promoters, immunoglobulin promoters, fragments thereof, or combinations of any of the foregoing. Examples of suitable regulated promoter control sequences include without limit those regulated by heat shock, metals, steroids, antibiotics, or alcohol. Non-limiting examples of tissue-specific promoters include B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPIIb promoter, ICAM-2 promoter, INF-β promoter, Mb promoter, NphsI promoter, OG-2 promoter, SP-B promoter, SYN1 promoter, and WASP promoter. The promoter sequence can be wild type or it can be modified for more efficient or efficacious expression.

The expression construct can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. Additional information can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., $3^{rd}$ edition, 2001.

(iii) Overexpression of Cellular Proteins Involved in Anti-Viral Responses

In alternate embodiments, the mammalian cell lines can be engineered to overexpress cellular proteins involved in host cell anti-viral responses. Non-limiting examples of proteins involved in anti-viral responses include double-stranded RNA-activated protein kinase R (PKR, which is also known as eukaryotic translation initiation factor 2-alpha kinase 2 or Eif2ak2), receptor interacting protein kinase 2 (RIPK2), interferons (e.g., Type I and Type II), interleukins (e.g., IL-1 and IL-6), tumor necrosis factor alpha, interferon regulatory factor 1, STATs, p53, activating transcription factor 3, NF-κB, eukaryotic initiation factor 2 (eIF2), inhibitors of apoptosis proteins (IAPs), and zinc-finger antiviral protein (ZAP). In specific embodiments, the cell lines can be engineered to overexpress PKR.

Overexpression can be achieved by introducing one or more exogenous copies of a nucleic acid sequence encoding the protein of interest. The sequence encoding the cellular protein of interest generally is operably linked to a Pol II promoter control sequence (see above). Multiple copies of the coding sequence can be linked in tandem and placed under the control of a single promoter control sequence. The sequence(s) encoding the protein of interest can be introduced into the cell lines as part of an expression construct (see above). Accordingly, the expression construct can be inserted into a chromosomal location or, alternatively, the expression construct can be extrachromosomal (e.g., episomal) for stable expression.

Overexpression also can be achieved by modifying the promoter control sequence of the endogenous chromosomal sequence encoding the protein of interest. For example, the endogenous promoter control sequence can be modified by inserting at least one exogenous "strong" promoter control sequence (i.e., having high affinity for RNA polymerase and/or associated factors) (examples of which are presented above). Alternatively, the sequence of the endogenous promoter control sequence can be modified to mimic "strong" promoter control sequences. Endogenous chromosomal sequences can be modified using targeting endonuclease-mediated genome modification techniques detailed below in section (III).

(b) Cell Types

The viral resistant cell lines disclosed herein are mammalian cell lines. In some embodiments, the cell lines having resistance to viral infection can be derived from Chinese hamster ovary (CHO) cells; mouse myeloma NS0 cells; baby hamster kidney (BHK) cells; mouse embryonic fibroblast 3T3 cells (NIH3T3); mouse B lymphoma A20 cells; mouse melanoma B16 cells; mouse myoblast C2C12 cells; mouse myeloma SP2/0 cells; mouse embryonic mesenchymal C3H-10T½ cells; mouse carcinoma CT26 cells, mouse prostate DuCuP cells; mouse breast EMT6 cells; mouse hepatoma Hepa1c1c7 cells; mouse myeloma J5582 cells; mouse epithelial MTD-1A cells; mouse myocardial MyEnd cells; mouse renal RenCa cells; mouse pancreatic RIN-5F cells; mouse melanoma X64 cells; mouse lymphoma YAC-1 cells; rat glioblastoma 9L cells; rat B lymphoma RBL cells; rat neuroblastoma B35 cells; rat hepatoma cells (HTC); buffalo rat liver BRL 3A cells; canine kidney cells (MDCK); canine mammary (CMT) cells; rat osteosarcoma D17 cells; rat monocyte/macrophage DH82 cells; monkey kidney SV-40 transformed fibroblast (COS 7) cells; monkey kidney CVI-76 cells; African green monkey kidney (VERO-76) cells; human embryonic kidney cells (HEK293, HEK293T); human cervical carcinoma cells (HELA); human lung cells (W138); human liver cells (Hep G2); human U2-OS osteosarcoma cells, human A549 cells, human A-431 cells, or human K562 cells. An extensive list of mammalian cell lines may be found in the American Type Culture Collection catalog (ATCC, Manassas, Va.). In other embodiments, the cell lines with viral resistance are non-human, mammalian cell lines. In further embodiments, the cell lines with viral resistance are non-human, non-mouse, mammalian cell lines. In certain embodiments, the cell lines with viral resistance are CHO cell lines. Numerous CHO cell lines are available from ATCC. Suitable CHO cell lines include, but are not limited to, CHO-K1 cells and derivatives thereof.

In various embodiments, the cell lines can be deficient in glutamine synthase (GS), dihydrofolate reductase (DHFR), hypoxanthine-guanine phosphoribosyltransferase (HPRT), or a combination thereof. For example, the chromosomal sequences encoding GS, DHFR, and/or HPRT can be inactivated. In specific embodiments, all chromosomal sequences encoding GS are inactivated in the cell lines.

(c) Viruses

The engineered mammalian cell lines having viral resistance can be resistant to a variety of mammalian viruses. The virus can be a DNA virus or an RNA virus, and the virus can be enveloped or non-enveloped ("naked"). Non-limiting examples of viruses that can bind to and enter mammalian cells via sialic acid receptors include parvoviruses, reoviruses, rotaviruses, influenza viruses, adeno-associated virus, calicivirus, parainfluenza virus, rubella virus, coronavirus, norovirus, encephalomyocarditis virus, and polyomaviruses. In some embodiments, the engineered mammalian cell lines are resistant to infection by at least one parvovirus. Non-limiting examples of suitable parvoviruses include minute virus of mouse (MVM) (which is also known as mouse minute virus (MMV) or rodent protoparvovirus 1), mouse parvovirus type-1 (MPV-1), mouse parvovirus type-2 (MPV-2), mouse parvovirus type-3 (MPV-3), porcine parvovirus 1, bovine parvovirus 1, and human parvovirus (e.g., human parvovirus B19, human parvovirus 4, human parvovirus 5, etc.). In particular embodiments, the parvovirus can be MVM. In other embodiments, the virus can be a reovirus, such as mammalian reovirus-3, mammalian orthoreovirus, avian orthoreovirus, and the like).

In some embodiments, the engineered mammalian cell lines having resistance to viral infection can also have resistance to infection by organisms in the order Mollicutes. In particular, the cell lines disclosed herein can be resistant to infection by the genera *mycoplasma* or *spiroplasma*.

(d) Optional Nucleic Acid Encoding Recombinant Protein

In some embodiments, the mammalian cell lines having resistance to viral infection can further comprise at least one nucleic acid encoding a recombinant protein. In general, the recombinant protein is heterologous, meaning that the protein is not native to the cell. The recombinant protein may be, without limit, a therapeutic protein chosen from an antibody, a fragment of an antibody, a monoclonal antibody, a humanized antibody, a humanized monoclonal antibody, a chimeric antibody, an IgG molecule, an IgG heavy chain, an IgG light chain, an IgA molecule, an IgD molecule, an IgE molecule, an IgM molecule, a vaccine, a growth factor, a cytokine, an interferon, an interleukin, a hormone, a clotting (or coagulation) factor, a blood component, an enzyme, a therapeutic protein, a nutraceutical protein, a functional fragment or functional variant of any of the forgoing, or a fusion protein comprising any of the foregoing proteins and/or functional fragments or variants thereof.

In some embodiments, the nucleic acid encoding the recombinant protein can be linked to sequence encoding hypoxanthine-guanine phosphoribosyltransferase (HPRT), dihydrofolate reductase (DHFR), and/or glutamine synthase (GS), such that HPRT, DHFR, and/or GS may be used as an amplifiable selectable marker. The nucleic acid encoding the recombinant protein also can be linked to sequence encoding at least one antibiotic resistance gene and/or sequence encoding marker proteins such as fluorescent proteins. In some embodiments, the nucleic acid encoding the recombinant protein can be part of an expression construct. As detailed elsewhere expression constructs or vectors can comprise additional expression control sequences (e.g., enhancer sequences, Kozak sequences, polyadenylation sequences, transcriptional termination sequences, etc.), selectable marker sequences, origins of replication, and the like. Additional information can be found in Ausubel et al. 2003, supra, and Sambrook & Russell, 2001, supra.

In some embodiments, the nucleic acid encoding the recombinant protein can be located extrachromosomally. That is, the nucleic acid encoding the recombinant protein can be transiently expressed from a plasmid, a cosmid, an artificial chromosome, a minichromosome, or another extra-chromsomal construct. In other embodiments, the nucleic acid encoding the recombinant protein can be chromosomally integrated into the genome of the cell. The integration can be random or targeted. Accordingly, the recombinant protein can be stably expressed. In some iterations of this embodiment, the nucleic acid sequence encoding the recombinant protein can be operably linked to an appropriate heterologous expression control sequence (i.e., promoter). In other iterations, the nucleic acid sequence encoding the recombinant protein can be placed under control of an endogenous expression control sequence. The nucleic acid sequence encoding the recombinant protein can be integrated into the genome of the cell line using homologous recombination, targeting endonuclease-mediated genome editing, viral vectors, transposons, plasmids, and other well-known means. Additional guidance can be found in Ausubel et al. 2003, supra and Sambrook & Russell, 2001, supra.

(e) Compositions

In certain embodiments, the mammalian cell lines engineered to exhibit viral resistance can be part of a composition, which also comprises at least one virus. The composition, therefore comprises the engineered cell line (optionally further comprising a nucleic acid encoding a recombinant protein) disclosed herein and a virus, wherein entry and/or propagation of the at least one virus is reduced or eliminated in the engineered mammalian cell line. Thus, the cells in the composition are able to propagate, but virus in the composition is unable to propagate because its entry and/or replication within the cells is reduced or eliminated. The composition can further comprise at least one cell growth medium to support growth of the engineered mammalian cell line cells. In some instances the cell growth medium is an animal component-free medium.

(f) Exemplary Embodiments

In specific embodiments, the mammalian cell lines having viral resistance are CHO cell lines. The viral resistant CHO cell lines can be resistant to infection by minute virus of mouse (MVM) (which is also known as mouse minute virus (MMV) or rodent protoparvovirus 1) and/or mammalian reovirus 3. Specifically, the genetically modified CHO cell lines have increased resistance to MVM or reovirus-3 infection as compared to unmodified parental CHO cell lines. In some embodiments, the unmodified parental cell line is a CHO (GS−/−) cell line.

The viral resistant CHO cell lines comprise at least one inactivated chromosomal sequence encoding COSMC, Slc35A1, C1GalT1, St3Gal1, St3Gal2, St3Gal3, St3Gal4, St3Gal5, and/or St3Gal6. In some embodiments, all copies of chromosomal sequences encoding COSMC, Slc35A1, C1GalT1, St3Gal1, St3Gal2, St3Gal3, St3Gal4, St3Gal5, and/or St3Gal6 are inactivated or knocked out in the CHO cell lines. In other embodiments, CHO cells comprising inactivated chromosomal sequenced encoding COSMC, Slc35A1, C1GalT1, St3Gal1, St3Gal2, St3Gal3, St3Gal4, St3Gal5, and/or St3Gal6 further comprise inactivated chromosomal sequences encoding Mgat1, Mgat2, Mgat3, Mgat4, and/or Mgat5. In further embodiments, CHO cells comprising inactivated chromosomal sequenced encoding St3Gal1, St3Gal2, St3Gal3, St3Gal4, St3Gal5, and/or St3Gal6 are further engineered to overexpress St6Gal 1, St6Gal 2, St6GalNac1, St6GalNac2, St6GalNac3, ST6GalNac4, St6GalNac5, and/or St6GalNac6.

(II) Methods for Reducing or Preventing Viral Contamination

Another aspect of the present disclosure encompasses methods for reducing or preventing viral contamination of a recombinant protein product, or reducing the risk of viral contamination of a biologic production system. In general, the methods comprise providing engineered mammalian cell lines in which entry and/or propagation of at least one the virus is reduced or eliminated, and using said cell lines for production of the recombinant protein. The engineered mammalian cell lines are detailed above in sections (I). The engineered mammalian cell lines exhibit increased resistance to viral infection as compared to unmodified parental cell lines. The engineered mammalian cell lines exhibit resistant to viruses described in section (I)(c). Suitable recombinant proteins are described in section (I)(d). Means for producing or manufacturing recombinant proteins are well known in the field (see, e.g., "*Biopharmaceutical Production Technology*", Subramanian (ed), 2012, Wiley-VCH; ISBN: 978-3-527-33029-4). In specific embodiments, the engineered mammalian cell lines are genetically modified to comprise at least one modified chromosomal sequence such that the cell line is resistant to viral infection.

In general, use of the engineered mammalian cell lines disclosed herein reduces the ability of viruses to replicate in a fermenter or other bioproduction vessel such that the level of replicatable virus is at trace level or, ideally, at a level that is not detectable by industry standard best practices. Suitable methods include nucleic acid detection methods (e.g., Southern blotting to detect viral nucleic acids, PCR or RT-PCR to detect viral nucleic acids, sequencing methods, and the like), antibody-based techniques (e.g., Western immunoblotting using anti-viral protein antibodies, ELISA methods, and so forth), and microscopic techniques (e.g., cytopathic effect assays, electron microscopy to detect viral particles, etc.).

(III) Methods for Preparing Viral Resistant Cell Lines

Yet another aspect of the present disclosure provides methods for preparing viral resistant cells having altered cell surface receptors, as detailed above in section (I)(a)(i). Chromosomal sequences encoding enzymes or proteins involved in the synthesis of glycan chains can be knocked-down or knocked-out using a variety of techniques to generate the viral resistant cell lines. In some embodiments, the viral resistant cell lines can be prepared by a targeting endonuclease-mediated genome modification process. In other embodiments, the viral resistant cell lines can be prepared by RNA interference-mediated mechanisms. In still other embodiments, the viral resistant cell lines can be prepared by site-specific recombination systems, random mutagenesis, or other methods known in the art.

(a) Targeting Endonuclease-Mediated Genome Editing

Targeting endonucleases can be used to modify (i.e., inactivate or alter) specific chromosomal sequences of interest. A specific chromosomal sequence can be inactivated by introducing into a cell a targeting endonuclease or a nucleic encoding the targeting endonuclease, which targets a specific chromosomal sequence. In one embodiment, the targeting endonuclease recognizes and binds the specific chromosomal sequence and introduces a double-stranded break that is repaired by a non-homologous end-joining (NHEJ) repair process. Because NHEJ is error prone, a deletion, insertion, and/or substitution of at least one nucleotide may occur, thereby disrupting the reading frame of the chromosomal sequence such that no protein product is produced. In another embodiment, the targeting endonucleases can also be used to alter a chromosomal sequence via a homologous recombination reaction by co-introducing a polynucleotide having substantial sequence identity with a portion of the targeted chromosomal sequence. The double-stranded break introduced by the targeting endonuclease is repaired by a homology-directed repair process such that the chromosomal sequence is exchanged with the polynucleotide in a manner that results in the chromosomal sequence being changed or altered.

A variety of targeting endonucleases can be used to modify the chromosomal sequence(s) of interest. The targeting endonuclease can be a naturally-occurring protein or an engineered protein. Suitable targeting endonucleases include, without limit, zinc finger nucleases (ZFNs), CRISPR/Cas endonucleases, transcription activator-like effector (TALE) nucleases (TALENs), meganucleases, site-specific endonucleases, and artificial targeted DNA double strand break inducing agents.

(i) Zinc Finger Nucleases

In specific embodiments, the targeting endonuclease can be a zinc finger nuclease (ZFN). ZFNs bind to a specific targeted sequence and introduce a double-stranded break into the targeted sequence. Typically, a ZFN comprises a DNA binding domain (i.e., zinc fingers) and a cleavage domain (i.e., nuclease), each of which is described below.

DNA Binding Domain.

A DNA binding domains or the zinc fingers can be engineered to recognize and bind to any nucleic acid sequence of choice. See, for example, Beerli et al. (2002) Nat. Biotechnol. 20:135-141; Pabo et al. (2001) Ann. Rev. Biochem. 70:313-340; Isalan et al. (2001) Nat. Biotechnol. 19:656-660; Segal et al. (2001) Curr. Opin. Biotechnol. 12:632-637; Choo et al. (2000) Curr. Opin. Struct. Biol. 10:411-416; Zhang et al. (2000) J. Biol. Chem. 275(43): 33850-33860; Doyon et al. (2008) Nat. Biotechnol. 26:702-708; and Santiago et al. (2008) Proc. Natl. Acad. Sci. USA 105:5809-5814. An engineered zinc finger binding domain may have a novel binding specificity compared to a naturally-occurring zinc finger protein. Engineering methods include, but are not limited to, rational design and various types of selection. Rational design includes, for example, using databases comprising doublet, triplet, and/or quadruplet nucleotide sequences and individual zinc finger amino acid sequences, in which each doublet, triplet or quadruplet nucleotide sequence is associated with one or more amino acid sequences of zinc fingers which bind the particular triplet or quadruplet sequence. See, for example, U.S. Pat. Nos. 6,453,242 and 6,534,261, the disclosures of which are incorporated by reference herein in their entireties. As an example, the algorithm of described in U.S. Pat. No. 6,453, 242 can be used to design a zinc finger binding domain to target a preselected sequence. Alternative methods, such as rational design using a nondegenerate recognition code table may also be used to design a zinc finger binding domain to target a specific sequence (Sera et al. (2002) Biochemistry 41:7074-7081). Publically available web-based tools for identifying potential target sites in DNA sequences as well as designing zinc finger binding domains are known in the art. For example, tools for identifying potential target sites in DNA sequences can be found at http://www.zincfinger-tools.org. Tools for designing zinc finger binding domains can be found at http://zifit.partners.org/ZiFiT. (See also, Mandell et al. (2006) Nuc. Acid Res. 34:W516-W523; Sander et al. (2007) Nuc. Acid Res. 35:W599-W605.)

A zinc finger binding domain can be designed to recognize and bind a DNA sequence ranging from about 3 nucleotides to about 21 nucleotides in length. In one embodiment, the zinc finger binding domain can be designed to recognize and bind a DNA sequence ranging from about 9 to about 18 nucleotides in length. In general, the zinc finger binding domains of the zinc finger nucleases used herein comprise at least three zinc finger recognition regions or zinc fingers, wherein each zinc finger binds 3 nucleotides. In one embodiment, the zinc finger binding domain comprises four zinc finger recognition regions. In another embodiment, the zinc finger binding domain comprises five zinc finger recognition regions. In still another embodiment, the zinc finger binding domain comprises six zinc finger recognition regions. A zinc finger binding domain can be designed to bind to any suitable target DNA sequence. See for example, U.S. Pat. Nos. 6,607,882; 6,534,261 and 6,453,242, the disclosures of which are incorporated by reference herein in their entireties.

Exemplary methods of selecting a zinc finger recognition region include phage display and two-hybrid systems, which are described in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237, each of which is incorporated by reference herein in its entirety. In addition, enhancement of binding specificity for zinc finger binding domains has been described, for example, in WO 02/077227, the entire disclosure of which is incorporated herein by reference.

Zinc finger binding domains and methods for design and construction of fusion proteins (and polynucleotides encoding same) are known to those of skill in the art and are described in detail in, for example, U.S. Pat. No. 7,888,121, which is incorporated by reference herein in its entirety. Zinc finger recognition regions and/or multi-fingered zinc finger proteins can be linked together using suitable linker sequences, including for example, linkers of five or more amino acids in length. See, U.S. Pat. Nos. 6,479,626; 6,903,185; and 7,153,949, the disclosures of which are incorporated by reference herein in their entireties, for non-limiting examples of linker sequences of six or more amino acids in length. The zinc finger binding domain described herein may include a combination of suitable linkers between the individual zinc fingers of the protein.

In some embodiments, the zinc finger nuclease further comprises a nuclear localization signal or sequence (NLS). A NLS is an amino acid sequence which facilitates targeting the zinc finger nuclease protein into the nucleus to introduce a double stranded break at the target sequence in the chromosome. Nuclear localization signals are known in the art. See, for example, Makkerh et al. (1996) Current Biology 6:1025-1027.

Cleavage Domain.

A zinc finger nuclease also includes a cleavage domain. The cleavage domain portion of the zinc finger nuclease can be obtained from any endonuclease or exonuclease. Non-limiting examples of endonucleases from which a cleavage domain can be derived include, but are not limited to, restriction endonucleases and homing endonucleases. See, for example, New England Biolabs Catalog or Belfort et al. (1997) Nucleic Acids Res. 25:3379-3388. Additional enzymes that cleave DNA are known (e.g., S1 Nuclease; mung bean nuclease; pancreatic DNase I; micrococcal nuclease; yeast HO endonuclease). See also Linn et al. (eds.) Nucleases, Cold Spring Harbor Laboratory Press, 1993. One or more of these enzymes (or functional fragments thereof) can be used as a source of cleavage domains.

A cleavage domain also can be derived from an enzyme or portion thereof, as described above, that requires dimerization for cleavage activity. Two zinc finger nucleases can be required for cleavage, as each nuclease comprises a monomer of the active enzyme dimer. Alternatively, a single zinc finger nuclease can comprise both monomers to create an active enzyme dimer. As used herein, an "active enzyme dimer" is an enzyme dimer capable of cleaving a nucleic acid molecule. The two cleavage monomers can be derived from the same endonuclease (or functional fragments thereof), or each monomer can be derived from a different endonuclease (or functional fragments thereof).

When two cleavage monomers are used to form an active enzyme dimer, the recognition sites for the two zinc finger nucleases are preferably disposed such that binding of the two zinc finger nucleases to their respective recognition sites places the cleavage monomers in a spatial orientation to each other that allows the cleavage monomers to form an active enzyme dimer, e.g., by dimerizing. As a result, the near edges of the recognition sites can be separated by about 5 to about 18 nucleotides. For instance, the near edges can be separated by about 5, 6, 7, 8, 9, 10, 11, 12, 13, 14, 15, 16, 17 or 18 nucleotides. It will however be understood that any integral number of nucleotides or nucleotide pairs can intervene between two recognition sites (e.g., from about 2 to about 50 nucleotide pairs or more). The near edges of the recognition sites of the zinc finger nucleases, such as for example those described in detail herein, can be separated by 6 nucleotides. In general, the site of cleavage lies between the recognition sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31978-31982. Thus, a zinc finger nuclease can comprise the cleavage domain from at least one Type IIS restriction enzyme and one or more zinc finger binding domains, which may or may not be engineered. Exemplary Type IIS restriction enzymes are described for example in International Publication WO 07/014,275, the disclosure of which is incorporated by reference herein in its entirety. Additional restriction enzymes also contain separable binding and cleavage domains, and these also are contemplated by the present disclosure. See, for example, Roberts et al. (2003) Nucleic Acids Res. 31:418-420.

An exemplary Type IIS restriction enzyme, whose cleavage domain is separable from the binding domain, is FokI. This particular enzyme is active as a dimer (Bitinaite et al. (1998) Proc. Natl. Acad. Sci. USA 95: 10, 570-10, 575). Accordingly, for the purposes of the present disclosure, the portion of the FokI enzyme used in a zinc finger nuclease is considered a cleavage monomer. Thus, for targeted double-stranded cleavage using a FokI cleavage domain, two zinc finger nucleases, each comprising a FokI cleavage monomer, can be used to reconstitute an active enzyme dimer. Alternatively, a single polypeptide molecule containing a zinc finger binding domain and two FokI cleavage monomers can also be used.

In certain embodiments, the cleavage domain comprises one or more engineered cleavage monomers that minimize or prevent homodimerization. By way of non-limiting example, amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains. Exemplary engineered cleavage monomers of FokI that form obligate heterodimers include a pair in which a first cleavage monomer includes mutations at amino acid residue positions 490 and 538 of FokI and a second cleavage monomer that includes mutations at amino-acid residue positions 486 and 499.

Thus, in one embodiment of the engineered cleavage monomers, a mutation at amino acid position 490 replaces Glu (E) with Lys (K); a mutation at amino acid residue 538 replaces Iso (I) with Lys (K); a mutation at amino acid residue 486 replaces Gln (Q) with Glu (E); and a mutation at position 499 replaces Iso (I) with Lys (K). Specifically, the engineered cleavage monomers can be prepared by mutating positions 490 from E to K and 538 from I to K in one cleavage monomer to produce an engineered cleavage monomer designated "E490K:I538K" and by mutating positions 486 from Q to E and 499 from I to K in another cleavage monomer to produce an engineered cleavage monomer designated "Q486E:I499K." The above described engineered cleavage monomers are obligate heterodimer mutants in which aberrant cleavage is minimized or abolished. Engineered cleavage monomers can be prepared using a suitable method, for example, by site-directed mutagenesis of wild-type cleavage monomers (FokI) as described in U.S. Pat. No. 7,888,121, which is incorporated herein in its entirety.

Additional Domains.

In some embodiments, the zinc finger nuclease further comprises at least one nuclear localization sequence (NLS). A NLS is an amino acid sequence which facilitates targeting the zinc finger nuclease protein into the nucleus to introduce a double stranded break at the target sequence in the chromosome. Nuclear localization signals are known in the art (see, e.g., Lange et al., J. Biol. Chem., 2007, 282:5101-5105). For example, in one embodiment, the NLS can be a monopartite sequence, such as PKKKRKV (SEQ ID NO: 1) or PKKKRRV (SEQ ID NO: 2). In another embodiment, the NLS can be a bipartite sequence. In still another embodiment, the NLS can be KRPAATKKAGQAKKKK (SEQ ID NO: 3). The NLS can be located at the N-terminus, the C-terminus, or in an internal location of the protein.

In additional embodiments, the zinc finger nuclease can also comprise at least one cell-penetrating domain. In one embodiment, the cell-penetrating domain can be a cell-penetrating peptide sequence derived from the HIV-1 TAT protein. As an example, the TAT cell-penetrating sequence can be GRKKRRQRRRPPQPKKKRKV (SEQ ID NO:4). In another embodiment, the cell-penetrating domain can be TLM (PLSSIFSRIGDPPKKKRKV; SEQ ID NO: 5), a cell-penetrating peptide sequence derived from the human hepatitis B virus. In still another embodiment, the cell-penetrating domain can be MPG (GALFLGWLGAAGSTMGAPKKKRKV; SEQ ID NO: 6 or GALFLGFLGAAGSTMGAWSQPKKKRKV; SEQ ID NO: 7). In an additional embodiment, the cell-penetrating domain can be Pep-1 (KETWWETWWTEWSQPKKKRKV; SEQ ID NO: 8), VP22, a cell penetrating peptide from Herpes simplex virus, or a polyarginine peptide sequence. The cell-penetrating domain can be located at the N-terminus, the C-terminus, or in an internal location of the zinc finger nuclease.

In still other embodiments, the zinc finger nuclease can further comprise at least one marker domain. Non-limiting examples of marker domains include fluorescent proteins, purification tags, and epitope tags. In one embodiment, the marker domain can be a fluorescent protein. Non limiting examples of suitable fluorescent proteins include green fluorescent proteins (e.g., GFP, GFP-2, tagGFP, turboGFP, EGFP, Emerald, Azami Green, Monomeric Azami Green, CopGFP, AceGFP, ZsGreen1), yellow fluorescent proteins (e.g. YFP, EYFP, Citrine, Venus, YPet, PhiYFP, ZsYellow1), blue fluorescent proteins (e.g. EBFP, EBFP2, Azurite, mKalama1, GFPuv, Sapphire, T-sapphire), cyan fluorescent proteins (e.g. ECFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), and orange fluorescent proteins (mOrange, mKO, Kusabira-Orange, Monomeric Kusabira-Orange, mTangerine, tdTomato) or any other suitable fluorescent protein. In another embodiment, the marker domain can be a purification tag and/or an epitope tag. Suitable tags include, but are not limited to, glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6×His, biotin carboxyl carrier protein (BCCP), and calmodulin. The marker domain can be located at the N-terminus, the C-terminus, or in an internal location of the zinc finger nuclease.

The marker domain can be linked to the zinc finger nuclease by a 2A peptide (Szymczak et al., 2004, Nat. Biotechnol., 589(5):589-94). The 2A peptide was originally characterized in positive-strand RNA viruses, which produce a polyprotein that is "cleaved" during translation into mature individual proteins. More specifically, the 2A peptide region (~20 amino acids) mediates "cleavage" at its own C-terminus to release itself from the downstream region of the polyprotein. In general, a 2A peptide sequence terminates with a glycine and a proline residue. During translation of a 2A peptide, the ribosome pauses after the glycine residue, resulting in release of the nascent polypeptide chain. Translation resumes, with the proline residue of the 2A sequence becoming the first amino acid of the downstream protein.

(ii) CRISPR/Cas Endonucleases

In other embodiments, the targeting endonuclease can be a CRISPR/Cas endonuclease. CRISPR/Cas endonucleases are RNA-guided endonucleases derived from CRISPR/Cas systems. Bacteria and archaea have evolved an RNA-based adaptive immune system that uses CRISPR (clustered regularly interspersed short palindromic repeat) and Cas (CRISPR-associated) proteins to detect and destroy invading viruses or plasmids. CRISPR/Cas endonucleases can be programmed to introduce targeted site-specific double-strand breaks by providing target-specific synthetic guide RNAs (Jinek et al., 2012, Science, 337:816-821).

Endonuclease.

The CRISPR/Cas endonuclease can be derived from a CRISPR/Cas type I, type II, or type III system. Non-limiting examples of suitable CRISPR/Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966.

In one embodiment, the CRISPR/Cas endonuclease is derived from a type II CRISPR/Cas system. In exemplary embodiments, the CRISPR/Cas endonuclease is derived from a Cas9 protein. The Cas9 protein can be from *Streptococcus pyogenes, Streptococcus thermophilus, Streptococcus* sp., *Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina*. In one specific embodiment, the Cas9 protein is from *Streptococcus pyogenes*.

In general, CRISPR/Cas proteins comprise at least one RNA recognition and/or RNA binding domain. RNA recognition and/or RNA binding domains interact with the guide RNA such that the CRISPR/Cas protein is directed to a specific chromosomal or chromosomal sequence (i.e., target site). CRISPR/Cas proteins can also comprise nuclease domains (i.e., DNase or RNase domains), DNA binding domains, helicase domains, protein-protein interaction domains, dimerization domains, as well as other domains.

The CRISPR/Cas endonuclease can be derived from a wild type CRISPR/Cas protein, a modified CRISPR/Cas protein, or a fragment of a wild type or modified CRISPR/Cas protein. The CRISPR/Cas protein can be modified to increase nucleic acid binding affinity and/or specificity, alter an enzymatic activity, and/or change another property of the protein. For example, nuclease (i.e., DNase, RNase) domains of the CRISPR/Cas protein can be modified, deleted, or inactivated. The CRISPR/Cas protein can be truncated to remove domains that are not essential for the function of the protein. The CRISPR/Cas protein also can be truncated or modified to optimize the activity of the protein or an effector domain fused with the CRISPR/Cas protein.

In some embodiments, the CRISPR/Cas endonuclease can be derived from a wild type Cas9 protein or fragment thereof. In other embodiments, the CRISPR/Cas endonuclease can be derived from a modified Cas9 protein. For example, the amino acid sequence of the Cas9 protein can be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein.

In general, a Cas9 protein comprises at least two nuclease (i.e., DNase) domains. For example, a Cas9 protein can comprise a RuvC-like nuclease domain and a HNH-like nuclease domain. The RuvC and HNH domains work together to cut single strands to make a double-strand break in DNA (Jinek et al., Science, 337: 816-821). In one embodiment, the CRISPR-based endonuclease is derived from a Cas9 protein and comprises two function nuclease domains.

The target sites recognized by naturally occurring CRISPR/Cas systems typically having lengths of about 14-15 bp (Gong et al., Science, 339:819-823). The target site has no sequence limitation except that sequence complementary to the 5' end of the guide RNA (i.e., called a protospacer sequence) is immediately followed by (3' or downstream) a consensus sequence. This consensus sequence is also known as a protospacer adjacent motif (or PAM). Examples of PAM include, but are not limited to, NGG, NGGNG, and NNAGAAW (wherein N is defined as any nucleotide and W is defined as either A or T). At the typical length, only about 5-7% of the target sites would be unique within a target genome, indicating that off target effects could be significant. The length of the target site can be expanded by requiring two binding events. For example, CRISPR-based endonucleases can be modified such that they can only cleave one strand of a double-stranded sequence (i.e., converted to nickases). Thus, the use of a CRISPR-based nickase in combination with two different guide RNAs would essentially double the length of the target site, while still effecting a double stranded break.

In some embodiments, therefore, the Cas9-derived endonuclease can be modified to contain only one functional nuclease domain (either a RuvC-like or a HNH-like nuclease domain). For example, the Cas9-derived protein can be modified such that one of the nuclease domains is deleted or mutated such that it is no longer functional (i.e., the domain lacks nuclease activity). In some embodiments in which one of the nuclease domains is inactive, the Cas9-derived protein is able to introduce a nick into a double-stranded nucleic acid (such protein is termed a "nickase"), but not cleave the double-stranded DNA. For example, an aspartate to alanine (D10A) conversion in a RuvC-like domain converts the Cas9-derived protein into a "HNH" nickase. Likewise, a histidine to alanine (H840A) conversion (in some instances, the histidine is located at position 839) in a HNH domain converts the Cas9-derived protein into a "RuvC" nickase. Thus, for example, in one embodiment the Cas9-derived nickase has an aspartate to alanine (D10A) conversion in a RuvC-like domain. In another embodiment, the Cas9-derived nickase has a histidine to alanine (H840A or H839A) conversion in a HNH domain. The RuvC-like or HNH-like nuclease domains of the Cas9-derived nickase can be modified using well-known methods, such as site-directed mutagenesis, PCR-mediated mutagenesis, and total gene synthesis, as well as other methods known in the art.

Additional Domains.

The CRISPR/Cas endonuclease or nickase generally comprises at least one nuclear localization signal (NLS). For example, in one embodiment, the NLS can be a monopartite sequence, such as PKKKRKV (SEQ ID NO: 1) or PKKKRRV (SEQ ID NO: 2). In another embodiment, the NLS can be a bipartite sequence. In still another embodiment, the NLS can be KRPAATKKAGQAKKKK (SEQ ID NO: 3). The NLS can be located at the N-terminus, the C-terminus, or in an internal location of the protein.

In some embodiments, the CRISPR/Cas endonuclease or nickase can further comprise at least one cell-penetrating domain. The cell-penetrating domain can be a cell-penetrating peptide sequence derived from the HIV-1 TAT protein. As an example, the TAT cell-penetrating sequence can be GRKKRRQRRRPPQPKKKRKV (SEQ ID NO: 4). In another embodiment, the cell-penetrating domain can be TLM (PLSSIFSRIGDPPKKKRKV; SEQ ID NO: 5), a cell-penetrating peptide sequence derived from the human hepatitis B virus. In still another embodiment, the cell-penetrating domain can be MPG (GALFLGWLGAAGSTMGAPKKKRKV; SEQ ID NO: 6 or GALFLGFLGAAGSTMGAWSQPKKKRKV; SEQ ID NO: 7). In an additional embodiment, the cell-penetrating domain can be Pep-1 (KETWWETWWTEWSQPKKKRKV; SEQ ID NO: 8), VP22, a cell penetrating peptide from Herpes simplex virus, or a polyarginine peptide sequence. The cell-penetrating domain can be located at the N-terminus, the C-terminus, or in an internal location of the protein.

In still other embodiments, the CRISPR/Cas endonuclease or nickase can further comprise at least one marker domain. Non-limiting examples of marker domains include fluorescent proteins, purification tags, and epitope tags. In one embodiment, the marker domain can be a fluorescent protein. Non limiting examples of suitable fluorescent proteins include green fluorescent proteins (e.g., GFP, GFP-2, tagGFP, turboGFP, EGFP, Emerald, Azami Green, Monomeric Azami Green, CopGFP, AceGFP, ZsGreen1), yellow fluorescent proteins (e.g. YFP, EYFP, Citrine, Venus, YPet, PhiYFP, ZsYellow1), blue fluorescent proteins (e.g. EBFP, EBFP2, Azurite, mKalama1, GFPuv, Sapphire, T-sapphire), cyan fluorescent proteins (e.g. ECFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), and orange fluorescent proteins (mOrange, mKO, Kusabira-Orange, Monomeric Kusabira-Orange, mTangerine, tdTomato) or any other suitable fluorescent protein. In another embodiment, the marker domain can be a purification tag and/or an epitope tag. Suitable tags include, but are not limited to, glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6×His, biotin carboxyl carrier protein (BCCP), and calmodulin. The marker domain can be located at the N-terminus, the C-terminus, or in an internal location of the protein. The marker domain can be linked to the CRISPR/Cas endonuclease or nickase by a 2A peptide (Szymczak et al., 2004, Nat. Biotechnol., 589(5): 589-94).

Guide RNA.

The CRISPR/Cas endonuclease is guided to the targeted site by a guide RNA. A guide RNA interacts with both the CRISPR/Cas endonuclease and the target site in the chromosomal, at which site the CRISPR/Cas endonuclease or nickase cleaves at least one strand of the double-stranded sequence. The guide RNA can be introduced into the cell along with CRISPR/Cas endonuclease or nucleic acid encoding the CRISPR/Cas endonuclease. Alternatively, DNA encoding both the CRISPR/Cas endonuclease and the guide RNA can be introduced into the cell.

A guide RNA comprises three regions: a first region at the 5' end that is complementary to sequence at the target site, a second internal region that forms a stem loop structure, and a third 3' region that remains essentially single-stranded. The first region of each guide RNA is different such that each guide RNA guides a CRISPR/Cas endonuclease or nickase to a specific target site. The second and third regions (also called the scaffold region) of each guide RNA can be the same in all guide RNAs.

The first region of the guide RNA is complementary to sequence (i.e., protospacer sequence) at the target site such that the first region of the guide RNA can base pair with sequence at the target site. In general, there are no mismatches between the sequence of the first region of the guide RNA and the sequence at the target site (i.e., the complementarity is total). In various embodiments, the first region of the guide RNA can comprise from about 10 nucleotides to more than about 25 nucleotides. For example, the region of base pairing between the first region of the guide RNA and the target site in the chromosomal sequence can be about 10, 11, 12, 13, 14, 15, 16, 17, 18, 19, 20, 22, 23, 24, 25, or more than 25 nucleotides in length. In exemplary embodiments, the first region of the guide RNA is about 19 or 20 nucleotides in length.

The guide RNA also comprises a second region that forms a secondary structure. In some embodiments, the secondary structure comprises a stem (or hairpin) and a loop. The length of the loop and the stem can vary. For example, the loop can range from about 3 to about 10 nucleotides in length, and the stem can range from about 6 to about 20 base pairs in length. The stem can comprise one or more bulges of 1 to about 10 nucleotides. Thus, the overall length of the second region can range from about 16 to about 60 nucleotides in length. In an exemplary embodiment, the loop is about 4 nucleotides in length and the stem comprises about 12 base pairs.

The guide RNA also comprises a third region at the 3' end that remains essentially single-stranded. Thus, the third region has no complementarity to any chromosomal sequence in the cell of interest and has no complementarity to the rest of the guide RNA. The length of the third region can vary. In general, the third region is more than about 4 nucleotides in length. For example, the length of the third region can range from about 5 to about 60 nucleotides in length.

The combined length of the second and third regions (or scaffold) of the guide RNA can range from about 30 to about 120 nucleotides in length. In one aspect, the combined length of the second and third regions of the guide RNA range from about 70 to about 100 nucleotides in length.

In some embodiments, the guide RNA comprises one molecule comprising all three regions. In other embodiments, the guide RNA can comprise two separate molecules. The first RNA molecule can comprise the first region of the guide RNA and one half of the "stem" of the second region of the guide RNA. The second RNA molecule can comprise the other half of the "stem" of the second region of the guide RNA and the third region of the guide RNA. Thus, in this embodiment, the first and second RNA molecules each contain a sequence of nucleotides that are complementary to one another. For example, in one embodiment, the first and second RNA molecules each comprise a sequence (of about 6 to about 20 nucleotides) that base pairs to the other sequence to form a functional guide RNA.

(iii) Other Targeting Endonucleases

In further embodiments, the targeting endonuclease can be a meganuclease. Meganucleases are endodeoxyribonucleases characterized by long recognition sequences, i.e., the recognition sequence generally ranges from about 12 base pairs to about 40 base pairs. As a consequence of this requirement, the recognition sequence generally occurs only once in any given genome. Among meganucleases, the family of homing endonucleases named LAGLIDADG has become a valuable tool for the study of genomes and genome engineering (see, e.g., Arnould et al., 2011, Protein Eng Des Sel, 24(1-2):27-31). A meganuclease can be targeted to a specific chromosomal sequence by modifying its recognition sequence using techniques well known to those skilled in the art.

In additional embodiments, the targeting endonuclease can be a transcription activator-like effector (TALE) nuclease. TALEs are transcription factors from the plant pathogen *Xanthomonas* that can be readily engineered to bind new DNA targets. TALEs or truncated versions thereof may be linked to the catalytic domain of endonucleases such as FokI to create targeting endonuclease called TALE nucleases or TALENs (Sanjana et al., 2012, Nat Protoc, 7(1):171-192), In still other embodiments, the targeting endonuclease can be a site-specific endonuclease. In particular, the site-specific endonuclease can be a "rare-cutter" endonuclease whose recognition sequence occurs rarely in a genome. Alternatively, the site-specific endonuclease can be engineered to cleave a site of interest (Friedhoff et al., 2007, Methods Mol Biol 352:1110123). Generally, the recognition sequence of the site-specific endonuclease occurs only once in a genome. In alternate further embodiments, the targeting endonuclease can be an artificial targeted DNA double strand break inducing agent.

(iv) Optional Polynucleotide

The method for targeted genome modification can further comprise introducing into the cell at least one polynucleotide comprising a sequence having substantial sequence identity to a sequence on at least one side of the targeted cleavage site such that the double-stranded break introduced by the targeting endonuclease can be repaired by a homology-directed repair process and the sequence of the polynucleotide is exchanged with the endogenous chromosomal sequence, thereby modifying the endogenous chromosomal sequence. For example, the polynucleotide comprises a first sequence having substantial sequence identity to sequence on one side of the targeted cleavage site and a second sequence having substantial sequence identity to sequence on the other side of the targeted cleavage site. Alternatively, the polynucleotide comprises a first sequence having substantial sequence identity to sequence on one side of the targeted cleavage site and a second sequence having substantial sequence identity to a sequence located away from the targeted cleavage site. The sequence located away from the targeted cleavage site may be tens, hundreds, or thousands of nucleotides upstream or downstream of the targeted cleavage site.

The lengths of the first and second sequences in the polynucleotide that have substantial sequence identity to sequences in the targeted chromosomal sequence can and will vary. In general, each of the first and second sequences in the polynucleotide is at least about 10 nucleotides in length. In various embodiments, the polynucleotide sequences having substantial sequence identity with chromosomal sequences can be about 15 nucleotides, about 20 nucleotides, about 25 nucleotides, about 30 nucleotides, about 40 nucleotides, about 50 nucleotides, about 100 nucleotides, or more than 100 nucleotides in length.

The phrase "substantial sequence identity" means that the sequences in the polynucleotide have at least about 75% sequence identity with the chromosomal sequences of interest. In some embodiments, the sequences in the polynucleotide about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with the chromosomal sequences of interest.

The length of the polynucleotide can and will vary. For example, the polynucleotide can range from about 20 nucleotides in length up to about 200,000 nucleotides in length. In various embodiments, the polynucleotide ranges from about 20 nucleotides to about 100 nucleotides in length, from about 100 nucleotides to about 1000 nucleotides in length, from about 1000 nucleotides to about 10,000 nucleotides in length, from about 10,000 nucleotides to about 100,000 nucleotides in length, or from about 100,000 nucleotides to about 200,000 nucleotides in length.

Typically, the polynucleotide is DNA. The DNA can be single-stranded or double-stranded. The polynucleotide can be a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer. In certain embodiments, the polynucleotide is single-stranded. In exemplary embodiments, the polynucleotide is a single-stranded oligonucleotide comprising less than about 200 nucleotides.

In some embodiments, the polynucleotide further comprises a marker. Such a marker may enable screening for targeted integrations. In some embodiments, the marker is a restriction endonuclease site. In other embodiments the marker is a fluorescent protein, a purification tag, or an epitope tag. Non limiting examples of suitable fluorescent proteins include green fluorescent proteins (e.g., GFP, GFP-2, tagGFP, turboGFP, EGFP, Emerald, Azami Green, Monomeric Azami Green, CopGFP, AceGFP, ZsGreen1), yellow fluorescent proteins (e.g. YFP, EYFP, Citrine, Venus, YPet, PhiYFP, ZsYellow1), blue fluorescent proteins (e.g. EBFP, EBFP2, Azurite, mKalama1, GFPuv, Sapphire, T-sapphire), cyan fluorescent proteins (e.g. ECFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), and orange fluorescent proteins (mOrange, mKO, Kusabira-Orange, Monomeric Kusabira-Orange, mTangerine, tdTomato) or any other suitable fluorescent protein. In other embodiments, the marker can be a purification tag and/or an epitope tag. Exemplary tags include, but are not limited to, glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6×His, biotin carboxyl carrier protein (BCCP), and calmodulin.

(v) Delivery to the Cell

The method comprises introducing the targeting endonuclease into the cell of interest. The targeting endonuclease can be introduced into the cell as a purified isolated protein or as a nucleic acid encoding the targeting endonuclease. The nucleic acid may be DNA or RNA. In embodiments in which the encoding nucleic acid is mRNA, the mRNA may be 5' capped and/or 3' polyadenylated. In embodiments in which the encoding nucleic acid is DNA, the DNA may be linear or circular. The DNA may be part of a vector, wherein the encoding DNA may be operably linked to a suitable promoter. Those skilled in the art are familiar with appropriate vectors, promoters, other control elements, and means of introducing the vector into the cell of interest.

The targeting endonuclease molecule(s) and the optional polynucleotide(s) described above can be introduced into the cell by a variety of means. Suitable delivery means include microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In a specific embodiment, the targeting endonuclease molecule(s) and polynucleotides(s) are introduced into the cell by nucleofection.

In embodiments in which more than one targeting endonuclease molecule and more than one polynucleotide are introduced into a cell, the molecules can be introduced simultaneously or sequentially. For example, targeting endonuclease molecules, each specific for a targeted cleavage site (and optional polynucleotides) can be introduced at the same time. Alternatively, each targeting endonuclease molecule, as well as the optional polynucleotides(s) can be introduced sequentially.

The ratio of the targeting endonuclease molecule(s) to the optional polynucleotide(s) can and will vary. In general, the ratio of targeting endonuclease molecule(s) to polynucleotide(s) ranges from about 1:10 to about 10:1. In various embodiments, the ratio of the targeting endonuclease molecule(s) to polynucleotide(s) may be about 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, or 10:1. In one embodiment, the ratio is about 1:1.

(vi) Culturing the Cell

The method further comprises maintaining the cell under appropriate conditions such that the double-stranded break introduced by the targeting endonuclease can be repaired by (i) a non-homologous end-joining repair process such that the chromosomal sequence is modified by a deletion, insertion and/or substitution of at least one nucleotide or, optionally, (ii) a homology-directed repair process such that the chromosomal sequence is exchanged with the sequence of the polynucleotide such that the chromosomal sequence is modified. In embodiments in which nucleic acid(s) encoding the targeting endonuclease(s) is introduced into the cell, the method comprises maintaining the cell under appropriate conditions such that the cell expresses the targeting endonuclease(s).

In general, the cell is maintained under conditions appropriate for cell growth and/or maintenance. Suitable cell culture conditions are well known in the art and are described, for example, in Santiago et al. (2008) PNAS 105:5809-5814; Moehle et al. (2007) PNAS 104:3055-3060; Urnov et al. (2005) Nature 435:646-651; and Lombardo et al (2007) Nat. Biotechnology 25:1298-1306. Those of skill in the art appreciate that methods for culturing cells are known in the art and can and will vary depending on the cell type. Routine optimization may be used, in all cases, to determine the best techniques for a particular cell type.

During this step of the process, the targeting endonuclease(s) recognizes, binds, and creates a double-stranded break(s) at the targeted cleavage site(s) in the chromosomal sequence, and during repair of the double-stranded break(s) a deletion, insertion, and/or substitution of at least one nucleotide is introduced into the targeted chromosomal sequence. In specific embodiments, the targeted chromosomal sequence is inactivated.

Upon confirmation that the chromosomal sequence of interest has been modified, single cell clones can be isolated and genotyped (via DNA sequencing and/or protein analyses). Cells comprising one modified chromosomal sequence can undergo one or more additional rounds of targeted genome modification to modify additional chromosomal sequences (e.g., see Example 1).

(b) RNA Interference

In another embodiment, the viral resistant cell line can be prepared using an RNA interference (RNAi) agent that inhibits expression of a target mRNA or transcript. The RNAi agent can lead to cleavage of the target mRNA or transcript. Alternatively, the RNAi agent can prevent or disrupt translation of the target mRNA into protein.

In some embodiments, the RNAi agent can be a short interfering RNA (siRNA). In general, a siRNA comprises a double-stranded RNA molecule that ranges from about 15 to about 29 nucleotides in length. The siRNA can be about 16-18, 17-19, 21-23, 24-27, or 27-29 nucleotides in length. In a specific embodiment, the siRNA is about 21 nucleotides in length. The siRNA can optionally further comprise one or two single-stranded overhangs, e.g., a 3' overhang on one or both ends. The siRNA can be formed from two RNA molecules that hybridize together or, alternatively, can be generated from a short hairpin RNA (shRNA) (see below). In some embodiments, the two strands of the siRNA are completely complementary, such that no mismatches or bulges exist in the duplex formed between the two sequences. In other embodiments, the two strands of the siRNA are substantially complementary, such that one or more mismatches and/or bulges may exist in the duplex formed between the two sequences. In certain embodiments, one or both of the 5' ends of the siRNA have a phosphate group, while in other embodiments one or both of the 5' ends lack a phosphate group. In other embodiments, one or both of the 3' ends of the siRNA have a hydroxyl group, while in other embodiments one or both of the 5' ends lack a hydroxyl group.

One strand of the siRNA, which is referred to as the "antisense strand" or "guide strand," includes a portion that hybridizes with the target transcript. In certain embodiments, the antisense strand of the siRNA is completely complementary with a region of the target transcript, i.e., it hybridizes to the target transcript without a single mismatch or bulge over a target region between about 15 and about 29 nucleotides in length, preferably at least 16 nucleotides in length, and more preferably about 18-20 nucleotides in length. In other embodiments, the antisense strand is substantially complementary to the target region, i.e., one or more mismatches and/or bulges may exist in the duplex formed by the antisense strand and the target transcript. Typically, siRNAs are targeted to exonic sequences of the target transcript. Those of skill in the art are familiar with programs, algorithms, and/or commercial services that design siRNAs for target transcripts. An exemplary example is the Rosetta siRNA Design Algorithm (Rosetta Inpharmatics, North Seattle, Wash.) and MISSION® siRNA (Sigma-Aldrich, St. Louis, Mo.). The siRNA can be enzymatically synthesized in vitro using methods well known to those of skill in the art. Alternatively, the siRNA can be chemically synthesized using oligonucleotide synthesis techniques that are well known in the art.

In other embodiments, the RNAi agent can be a short hairpin RNA (shRNA). In general, a shRNA is an RNA molecule comprising at least two complementary portions that are hybridized or are capable of hybridizing to form a double-stranded structure sufficiently long to mediate RNA interference (as described above), and at least one single-stranded portion that forms a loop connecting the regions of the shRNA that form the duplex. The structure is also called a stem-loop structure, with the stem being the duplex portion. In some embodiments, the duplex portion of the structure is completely complementary, such that no mismatches or bulges exist in the duplex region of the shRNA.

In other embodiments, the duplex portion of the structure is substantially complementary, such that one or more mismatches and/or bulges exist in the duplex portion of the shRNA. The loop of the structure can be from about 1 to about 20 nucleotides in length, preferably from about 4 to about 10 about nucleotides in length, and more preferably from about 6 to about 9 nucleotides in length. The loop can be located at either the 5' or 3' end of the region that is complementary to the target transcript (i.e., the antisense portion of the shRNA).

The shRNA can further comprise an overhang on the 5' or 3' end. The optional overhang can be from about 1 to about 20 nucleotides in length, and more preferably from about 2 to about 15 nucleotides in length. In some embodiments, the overhang comprises one or more U residues, e.g., between about 1 and about 5 U residues. In some embodiments, the 5' end of the shRNA has a phosphate group, while in other embodiments it does not. In other embodiments, the 3' end of the shRNA has a hydroxyl group, while in other embodiments it does not. In general, shRNAs are processed into siRNAs by the conserved cellular RNAi machinery. Thus, shRNAs are precursors of siRNAs and are similarly capable of inhibiting expression of a target transcript that is complementary to a portion of the shRNA (i.e., the antisense portion of the shRNA). Those of skill in the art are familiar with the available resources (as detailed above) for the design and synthesis of shRNAs.

In still other embodiments, the RNAi agent can be an RNAi expression vector. Typically, an RNAi expression vector is used for intracellular (in vivo) synthesis of RNAi agents, such as siRNAs or shRNAs. In one embodiment, two separate, complementary siRNA strands are transcribed using a single vector containing two promoters, each of which directs transcription of a single siRNA strand (i.e., each promoter is operably linked to a template for the siRNA so that transcription may occur). The two promoters can be in the same orientation, in which case each is operably linked to a template for one of the complementary siRNA strands. Alternatively, the two promoters can be in opposite orientations, flanking a single template so that transcription for the promoters results in synthesis of two complementary siRNA strands. In another embodiment, the RNAi expression vector can contain a promoter that drives transcription of a single RNA molecule comprising two complementary regions, such that the transcript forms a shRNA.

Those of skill in the art will appreciate that it is preferable for siRNA and shRNA agents to be produced in vivo via the transcription of more than one transcription unit. Generally speaking, the promoters utilized to direct in vivo expression of the one or more siRNA or shRNA transcription units may be promoters for RNA polymerase III (Pol III). Certain Pol III promoters, such as U6 or H1 promoters, do not require cis-acting regulatory elements within the transcribed region, and thus, are preferred in certain embodiments. In other embodiments, promoters for Pol II can be used to drive expression of the one or more siRNA or shRNA transcription units. In some embodiments, tissue-specific, cell-specific, or inducible Pol II promoters can be used.

A construct that provides a template for the synthesis of siRNA or shRNA can be produced using standard recombinant DNA methods and inserted into any of a wide variety of different vectors suitable for expression in eukaryotic cells. Recombinant DNA techniques are described in Ausubel et al, 2003, supra and Sambrook & Russell, 2001, supra. Those of skill in the art also appreciate that vectors can comprise additional regulatory sequences (e.g., termination sequence, translational control sequence, etc.), as well selectable marker sequences. DNA plasmids are known in the art, including those based on pBR322, PUC, and so forth. Since many expression vectors already contain a suitable promoter or promoters, it may be only necessary to insert the nucleic acid sequence that encodes the RNAi agent of interest at an appropriate location with respect to the promoter(s). Viral vectors can also be used to provide intracellular expression of RNAi agents. Suitable viral vectors include retroviral vectors, lentiviral vectors, adenoviral vectors, adeno-associated virus vectors, herpes virus vectors, and so forth. In a specific embodiment, the RNAi expression vector is a shRNA lentiviral-based vector or lentiviral particle, such as that provided in MISSION® TRC shRNA products (Sigma-Aldrich).

The RNAi agents or RNAi expression vectors can be introduced into the cell using methods well known to those of skill in the art. Such techniques are described in Ausubel et al., 2003, supra or Sambrook & Russell, 2001, supra, for example. In certain embodiments, the RNAi expression vector, e.g., a viral vector, is stably integrated into the genome of the cell, such that Mgat1 expression is disrupted over subsequent cell generations.

(c) Site-Specific Recombination

In alternate embodiments, the viral resistance cell lines can be prepared using site-specific recombination techniques. For example, site-specific recombination techniques can be used to delete all or part of a chromosomal sequence of interest, or introduce single nucleotide polymorphisms (SNPs) into the chromosomal sequence of interest. In one embodiment, the chromosomal sequence of interest is targeted using a Cre-IoxP site-specific recombination system, a Flp-FRT site-specific recombination system, or variants thereof. Such recombination systems are commercially available, and additional teaching for these techniques is found in Ausubel et al., 2003, supra, for example.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As used herein, "deficient" refers to reduced or non-detectable levels of the targeted enzymes or proteins, or reduced or non-detectable activity of the targeted enzymes or proteins.

As used herein, the term "endogenous sequence" refers to a chromosomal sequence that is native to the cell.

The term "exogenous sequence" refers to a chromosomal sequence that is not native to the cell, or a chromosomal sequence that is moved to a different chromosomal location.

A "genetically modified" cell refers to a cell in which the genome has been modified, i.e., the cell contains at least chromosomal sequence that has been engineered to contain an insertion of at least one nucleotide, a deletion of at least one nucleotide, and/or a substitution of at least one nucleotide.

The terms "genome modification" and "genome editing" refer to processes by which a specific chromosomal sequence is changed such that the chromosomal sequence is modified. The chromosomal sequence may be modified to comprise an insertion of at least one nucleotide, a deletion of at least one nucleotide, and/or a substitution of at least one nucleotide. The modified chromosomal sequence is inactivated such that no product is made. Alternatively, the chromosomal sequence can be modified such that an altered product is made.

A "gene," as used herein, refers to a DNA region (including exons and introns) encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

The term "heterologous" refers to an entity that is not native to the cell or species of interest.

The terms "nucleic acid" and "polynucleotide" refer to a deoxyribonucleotide or ribonucleotide polymer, in linear or circular conformation. For the purposes of the present disclosure, these terms are not to be construed as limiting with respect to the length of a polymer. The terms can encompass known analogs of natural nucleotides, as well as nucleotides that are modified in the base, sugar and/or phosphate moieties. In general, an analog of a particular nucleotide has the same base-pairing specificity; i.e., an analog of A will base-pair with T. The nucleotides of a nucleic acid or polynucleotide may be linked by phosphodiester, phosphothioate, phosphoramidite, phosphorodiamidate bonds, or combinations thereof.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

The terms "polypeptide" and "protein" are used interchangeably to refer to a polymer of amino acid residues.

As used herein, the terms "target site" or "target sequence" refer to a nucleic acid sequence that defines a portion of a chromosomal sequence to be modified or edited and to which a targeting endonuclease is engineered to recognize and bind, provided sufficient conditions for binding exist.

The terms "upstream" and "downstream" refer to locations in a nucleic acid sequence relative to a fixed position. Upstream refers to the region that is 5' (i.e., near the 5' end of the strand) to the position and downstream refers to the region that is 3' (i.e., near the 3' end of the strand) to the position.

As used herein, "viral resistance" refers to the ability of cells to resist viral infection. More specifically, entry of a virus and/or propagation of a virus is reduced or eliminated in the engineered cell lines disclosed herein as compared to unmodified parental cell lines.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the GenBank website. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

As various changes could be made in the above-described cells and methods without departing from the scope of the invention, it is intended that all matter contained in the above description and in the examples given below, shall be interpreted as illustrative and not in a limiting sense.

EXAMPLES

The following examples illustrate certain aspects of the invention.

Example 1: Preparation of Targeted Gene Modified CHO Cell Lines

ZFN-mediated gene modification techniques were employed to inactivate (i.e., knock out) genes encoding enzymes or proteins involved in N- or O-linked glycosylation reactions. In general, pairs of ZFNs targeting specific sites within the coding region of the genes of interest were designed using a proprietary algorithm. ZFN expression constructs were prepared using standard procedures and ZFN mRNA was produced from ZFN plasmid DNA as described in COMPOZr® Knockout Zinc Finger Nuclease (ZFN) (Sigma-Aldrich) product information using in vitro transcription, mRNA poly-adenylation, and capping methods. Briefly, the plasmid ZFN DNA was linearized and purified using phenol/chloroform DNA extraction. Message-Max™ T7 ARCA-Capped Message Transcription Kit (Cell Script Inc.) was used to cap the linearized DNA. A Poly(A) Polymerase Tailing Kit (EpiCentre) was used to add a poly(A) tail. The ZFN mRNA was purified using the MEGAclear™ kit (Ambion). Parental cells were maintained as suspension cultures in EX-CELL® CHO CD Fusion media (Sigma-Aldrich). Cells were seeded at $0.5 \times 10^6$ cells/mL in bioreactor tubes one day prior to transfection. Typically, each transfection contained $1 \times 10^6$ cells in 150 μL growth media and 5 μg ZFN DNA or mRNA. Transfections were conducted by electroporation at 140 V and 950 μF in 0.2 cm cuvettes. Electroporated cells were placed in 2 mL growth media in a 6-well plate static culture.

On days 3 and 10 post-transfection, cells were removed from culture and genomic DNA was isolated using GeneElute™ Mammalian Genomic DNA Miniprep Kit (Sigma-Aldrich). ZFN-induced cleavage was verified using a Cel-1 nuclease assay, as described in CompoZr® Knockout ZFN product information. This assay is conducted to determine the efficiency of ZFN-mediated gene mutation as described previously (Miller et al., Nat. Biotechnol. 2007, 25:778-785). The assay detects alleles of the targeted locus that deviate from wild type as a result of non-homologous end joining (NHEJ)-mediated imperfect repair of ZFN-induced DNA double strand breaks. PCR amplification of the targeted region from a pool of ZFN-treated cells generates a mixture of wild type (WT) and mutant amplicons. Melting and reannealing of this mixture results in mismatches forming between heteroduplexes of the WT and mutant alleles. A DNA "bubble" formed at the site of mismatch is cleaved by the surveyor nuclease Cel-1, and the cleavage products can be resolved by gel electrophoresis.

Upon confirmation of ZFN activity, the ZFN transfected cells were single-cell cloned using limiting dilution. For this, cells were plated at an approximate density of about 0.5 cell/well using a mixture of 80% CHO serum-free cloning media, 20% conditioned media, and 4 mM L-glutamine. Clonality and growth were microscopically verified on days 7 and 14 post plating, respectively. Clones with growth were expanded and genotyped by PCR and DNA sequencing.

Mgat1 KO Cell Line.

Mgat1 adds GlnNac to the Man5GlcNAc2 N-linked glycan structure as part of complex N-glycan synthesis. A pair of ZFNs was designed to target 5'-AACAAGTTCAAGT-TCccagcaGCTGTGGTAGTGGAGGAC-3' (SEQ ID NO: 9; ZFN binding sites in upper case and the cleavage site in lower case) in the CHO Mgat1 gene. The parental cell line was CHOK1 (GS−/−) (Sigma Aldrich) in which glutamate synthetase was knocked out. This parental cell line produces wild type N- and O-glycan structures. The CHOK1 (GS−/−) cell lines was transfected with Mgat1 ZFN DNA essentially as detailed above. A Cel-1 assay confirmed the presence of two cleavage fragments, 220 and 197 bp, at both days 3 and 10 post-transfection, indicating ZFN activity. Single-cell clones were identified with deletions ranging from 2 bp to 55 bp in one allele (a second allele was not detected). This cell line produces truncated N-linked structures terminating with five mannose residues (i.e., Man5NeuAc2 glycoforms) and wild type O glycan structures.

COSMC KO Cell Line.

The most common second biosynthetic step in O-glycosylation is the core-1 elongation. Core-1 elongation is catalyzed by a single enzyme C1GalT1 (aka T-synthase) that requires a dedicated chaperone, COSMC, in order to function. COSMC is an ER protein that appears to bind specifically to T-synthase and ensures its full activity in the Golgi. To disrupt the COSMC gene, CHOK1 (GS−/−) cells were transfected with DNA or RNA encoding ZFNs designed to target sequence 5'-GCCTTCTCAGTGTTCCGGAaaagt-gTCCTGAACAAGGTGGGAT-3' (SEQ ID NO: 10) in the CHO COSMC gene. A Cel-1 nuclease assay confirmed the presence of three cleavage fragments (i.e., 318, 184, 134 bp) in the ZFN transfected cells. A single cell clone was isolated that had a 4 bp deletion in one allele of COSMC (a second allele was not detected). The cell line produces truncated (i.e., immature) O-glycan structures and wild type N-glycans.

COSMC/Mgat3 KO Cell Line.

A pair of ZFNs was designed to target 5'-TTCCTGGAC-CACTTCCCAcccggtGGCCGGCAGGATGGC-3' (SEQ ID NO: 11) in the coding region of Mgat3. The COSMC KO cell line, detailed above, was transfected with ZFN DNA as detailed above. After confirmation of ZFN cleavage, single cell clones were isolated. Sequencing revealed that the mutant clones had 9, 10, 11, or 41 bp deletions in the Mgat3 gene. This cell line produces wild type N-glycans and truncated O-glycans (i.e., is similar to the parental cell line).

COSMC/Mgat3/Mgat5 KO Cell Line.

The COSMC/Mgat3 KO cell line, detailed above, was transfected with plasmid DNA encoding ZFNs designed to target 5'-TTCTGCACTTCACCATCCAgcagcgGACTCA-GCCTGAGAGCAGCT-3' (SEQ ID NO: 12) in the coding region of Mgat5. A single cell clone was isolated that had a 129 bp deletion in the Mgat5 gene. This cell line produces N-glycans with less side branching and truncated O-glycans.

Example 2: Viral Infections and Viral Resistance Testing Assays

The above-described CHO cell lines were grown and tested for their ability to support or resist infection following challenge with the prototype MVM virus (strain MVMp). Briefly, cells were grown in the appropriate media and MVMp virus was added at a multiplicity of infection (MOI) of either 1 or 10, and infected cells incubated for an additional 24, 48 or 72 hours prior to assay. As controls, cells were grown and incubated without virus. Uninfected cells were also treated with the enzyme neuraminidase to remove terminal sialic acids from surface glycans (both N and O-linked) and subsequently infected at indicated MOIs.

Infected and non-infected cells were examined visually for the presence of cytopathic effect (CPE) and at the indicated time-points, cells were harvested by centrifugation. Viral DNA infectivity and production was screened using Southern blot analysis on total genomic DNA, and Western immunoblot analysis using an anti-viral protein antibody. For the Southern analysis, cell pellets from duplicate samples taken at 24 hr were harvested and total genomic DNA isolated. The DNA was quantitated via Nanodrop spectroscopy and samples were normalized to insure equaling loading on agarose gels for size fractionation. The size fractionated DNA was transferred onto charged membranes (Southern blotting), and the membrane probed for viral DNA synthesis using a $^{32}$P-labeled viral DNA probe. Quantification of the specific $^{32}$P-labeled viral double stranded DNA bands was acquired by phosphor imaging and relative values are reported in Table 1.

TABLE 1

Viral Levels

| Cell Line | MOI | Neuraminidase treatment | Viral DNA (relative value) |
|---|---|---|---|
| Wild type | 10 | | 133.35 |
| Wild type | 10 | Yes | 25.59 |
| Mgat1 KO | 10 | | 49.56 |
| COSMC KO | 10 | | 24.01 |
| Wild type | 10 | | 121.36 |
| Wild type | 10 | Yes | 31.38 |
| COSMC/Mgat3 KO | 10 | | 23.78 |
| COSMC/Mgat3/Mgat5 KO | 10 | | 28.87 |
| Wild type | 1 | | 36.28 |
| Wild type | 1 | Yes | 4.16 |
| Mgat1 KO | 1 | | 17.263 |
| COSMC KO | 1 | | 1.58 |
| Wild type | 1 | | 85.61 |
| Wild type | 1 | Yes | 11.65 |
| COSMC/Mgat3 KO | 1 | | 0.45 |
| COSMC/Mgat3/Mgat5 KO | 1 | | 0.54 |

For the Western analysis, cell pellets harvested at 24 hr were lysed in SDS buffers, and proteins were separated using SDS-PAGE. Post electrophoresis, proteins were transferred onto PVDF membranes, blocked and immunoblotted (Western immunoassay) for the presence of the viral NS1 protein using an anti-NS1 antibody. The level of viral protein detected via Western blotting is indicated in Table 2.

TABLE 2

Summary of Western Analysis

| Cell line | Glycan structures produced | Virus production |
|---|---|---|
| Wild type | Wild type O- and N-linked | +++++ at both MOIs |
| Wild type + neuraminidase | Removal of terminal sialic acid (O- and N-linked) | + at MOI = 10 |
| Mgat1 KO | Wild type O-linked; Truncated N-linked | +++ at both MOIs |
| COSMC KO | Wild type N-linked; Truncated O-linked | − at MOI = 1<br>+ at MOI = 10 |
| COSMC/Mgat3 KO | Truncated O-linked; Presumably wild type | − at MOI = 1<br>+ at MOI = 10 |
| COSMC/Mgat3/Mgat5 | Truncated O-linked; Modified N-linked (less side branching) | − at MOI = 1<br>+ at MOI = 10 |

When infected with the MVMp strain of the virus, the parental cell line CHOK1 (GS−/−) (i.e., with wild type glycan structures) showed classic infectivity and production of viral DNA and protein synthesis as expected. Viral DNA and viral protein products were evident 24 hours post infection when cells infected at either MOI. Strong production of viral products was seen at the latter time-points as well. Uninfected wild type cells showed no evidence of infection, as expected, regardless of the time-points.

When wild type cells were treated with the enzyme neuraminidase (NA) to remove cell surface sialic acid and cells subsequently infected with MVMp, a reduced production of virus (indicating reduction of the infection) was also observed (ranging from 5.32-fold at MOI=10 to 7.34-fold at MOI=1). While the NA treated cells still showed slight sensitivity to infection, it is known that CHO cells rapidly regenerate sialic acid (SA) structures following such treatment. Therefore, the low level of infection that was seen may be from cells that have regenerated terminal SA glycans and hence provide entry for the virus.

Viral infection of Mgat1 KO cells in which the CHO Mgat1 gene was inactivated and no Mgat1 enzyme was made, resulted in only a slight resistance (e.g., reduction of 2.1- to 2.7-fold, as measured by phosphor imaging of blots) to viral infection. Because this cell line has truncated N-glycans, these results suggest that higher order N-glycan receptors that have 2-3 linked sialic acids may play only a minor role in the initial viral capsid binding and viral entry into the cell.

When COSMC KO cells were infected with MVMp virus, this cell line showed significant resistance to viral infection. Fold resistance (when compared to the wild type cell line) ranged from 5.5 fold (MOI=10) to 190 fold (MOI=1). Additional gene knockout that targeted the Mgat3 gene (presumed to be a pseudogene in CHO cells) and the Mgat5 gene (responsible for higher order N-linked branching), gave similar results. Western blot analysis gave similar results, indicating that viral resistance occurs when O-glycan structures were truncated. These studies revealed that disruption of sialic acid receptors drastically reduced MVM binding and/or entry into the cells.

Example 3: Generation of Additional COSMC KO and Slc35A1 KO Cell Lines

New COSMC KO cell line clones were generated as described above in Example 1 using CHOK1 (GS−/−) cells and a pair of ZFNs designed to target sequence 5'-GCCT-TCTCAGTGTTCCGGAaaagtgTCCT-GAACAAGGTGGGAT-3' (SEQ ID NO: 10) in exon 2 of the CHO COSMC gene. A Cel-1 nuclease assay confirmed the presence of three cleavage fragments (i.e., 318, 184, 134 bp) in the ZFN transfected cells. Five single cell clones were isolated and sequencing revealed deletions of 1 to 12 bp, as shown below.

| Clone | Genotype |
|---|---|
| COSMC F07 | 2 bp deletion |
| COSMC G03 | 1 bp insertion |
| COSMC H04 | 1 bp insertion |
| COSMC A09 | 9 bp deletion |
| COSMC H05 | 12 bp deletion |

Clone F07 was further modified to express a human IgG using standard procedures. Of the many clones identified, two IgG producing clones were isolated (and identified as 71H1, 71C3) for further testing (see below).

The Slc35A1 gene, which codes for a nucleotide sugar transporter (CMP-sialic acid transporter), was knocked out in CHOK1 (GS−/−) cells using ZFNs designed to target 5'-AGCTTATACCGTAGCTTTaagataCACAAGGA-CAACAGCTAAA-3' (SEQ ID NO: 13) or ZFNs designed to target 5'-TTCAAGCTATACTGCTTGGCAGTGAT-GACTCTGGTGGCT-3' (SEQ ID NO: 17) in exon 1 of the CHO Slc35A1 gene. A Cel-1 nuclease assay confirmed the presence of two cleavage fragments in the ZFN transfected cells. One single cell clone (B12) was isolated and sequencing revealed a 1 bp deletion around the ZFN binding site. The Slc35A1 KO cell line forms N and O linked glycan structures without terminal sialic acid.

Staining with biotinylated *Maackia Amurensis* lectin II (MALII; 20 µg/mL) and Alexa Fluor 647-labeled streptavidin (5 µg/mL) revealed significantly reduced staining in the COSMC KO clone F07, COSMC KO clone G03, and Slc35A1 KO cell lines as compared to the parental cell line (indicating the absence of terminal sialic acid residues in the KO cell lines).

Example 4: Resistance of COSMC KO and Slc35A1 KO Cell Lines to MMV Virus

Wild-type (i.e., CHOZN GS−/−), COSMC KO (generated above in Examples 1 and 3), and Slc35A1 KO (generated above in Example 3) cells were infected with MVMp virus at a MOI of 0.3 essentially as described above in Example 2. Infection was assayed via Southern analysis (essentially as described above) and standard plaque assays.

Figure 2:
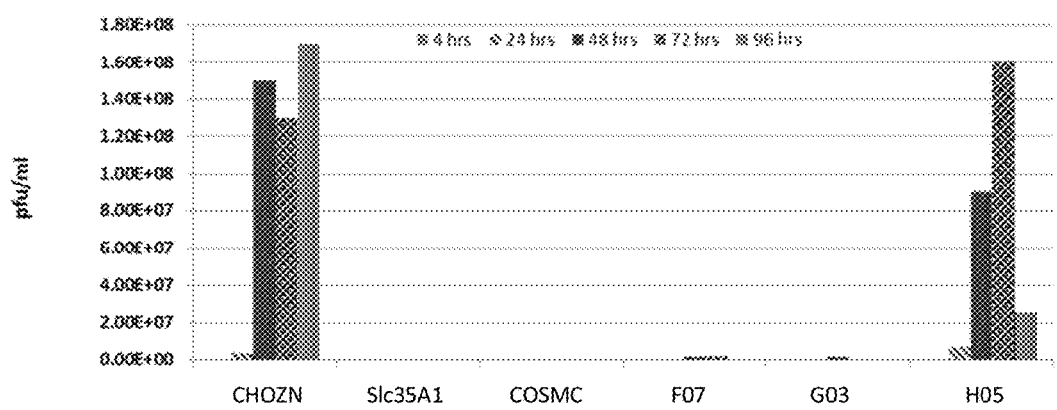
FIG. 2 shows a time course of MVM viral infection as detected by plaque assays. Plotted is the pfu/mL detected at 24, 48, 72 and 96 hours for wild-type cells (CHOZN), Slc35A1 KO, COSMC KO, COSMC KO clone F07, COSMC KO clone G03, and COSMC KO clone H05.

As shown in FIG. 1, the wild-type cells exhibited high levels of viral DNA, whereas Slc35A1 KO and COSMC KO cell lines had very low levels of viral DNA; COSMC F07 KO and COSMC G03 KO clones had low levels of viral DNA; and COSMC H05 FO clone, which had a 12 bp deletion, had levels of viral DNA similar to the parental cell line. Since the deletion in H05 was in-frame, it is not surprising that the cells exhibited viral sensitivity at near wild-type levels. The plaque assay results are shown in FIG. 2. Slc35A1 KO, COSMC KO, COSMC F07 KO, and COSMC G03 KO cells had extremely low viral levels.

Additional viral resistance testing was performed using wild-type (i.e., CHOZN GS−/−, also called 2E3), COSMC KO clones F07 and G03, and Slc35A1 KO clone B12. Cells were grown in media supplemented with 6 mM L-glutamine and infected with MMVp at a MOI of either 1 or 8 and incubated under suitable conditions. Samples of cells were removed at 0, 24, 48, 72, 96, and 120 hours; cell viability was assayed with trypan blue staining and MMV quantification was determined by qPCR.

Figure 3A:
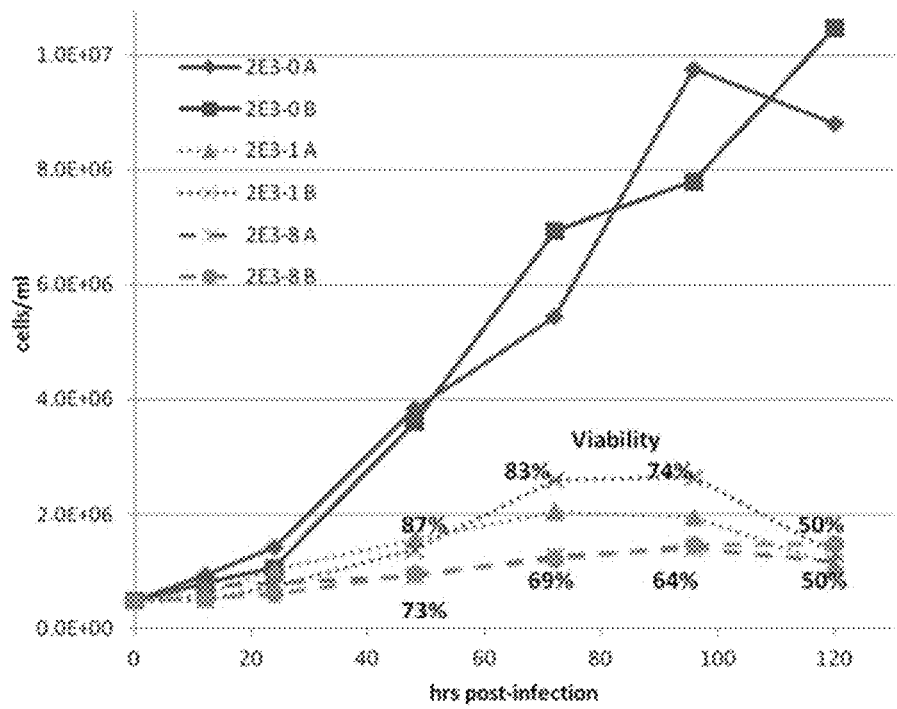
FIG. 3A illustrates the effect of MMV infection on wild-type (2E3) cell growth. Plotted is the number of viable cells (cells/ml) over the course of 120 hours in the absence (solid lines) and presence (broken lines) of MVM virus at MOI of 1 or 8.
Figure 3B:
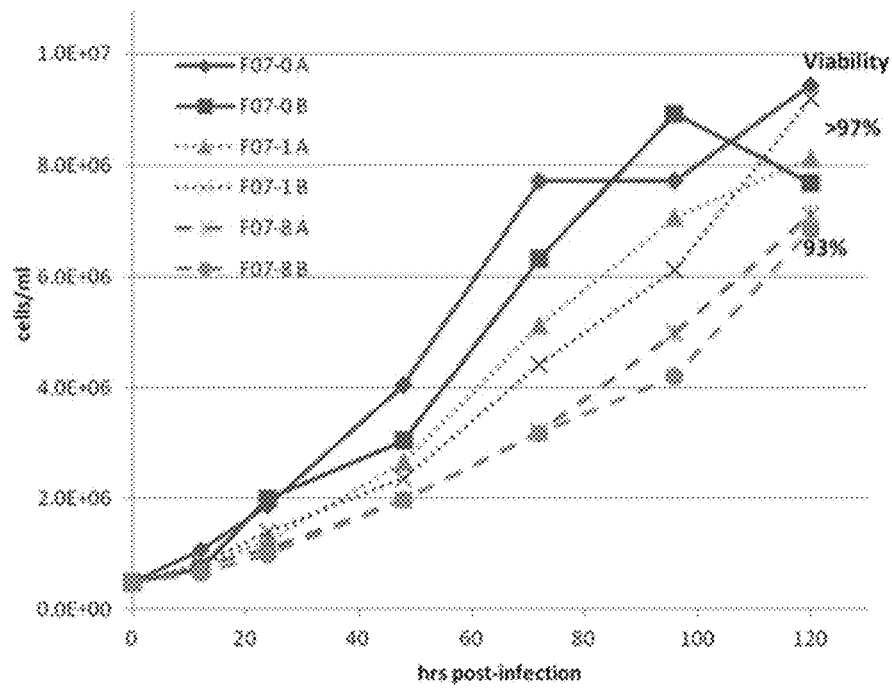
FIG. 3B shows the effect of MMV infection on COSMC KO clone F07 cell growth. Plotted is the number of viable cells (cells/ml) over the course of 120 hours in the absence (solid lines) and presence (broken lines) of MVM virus at MOI of 1 or 8.
Figure 4A:
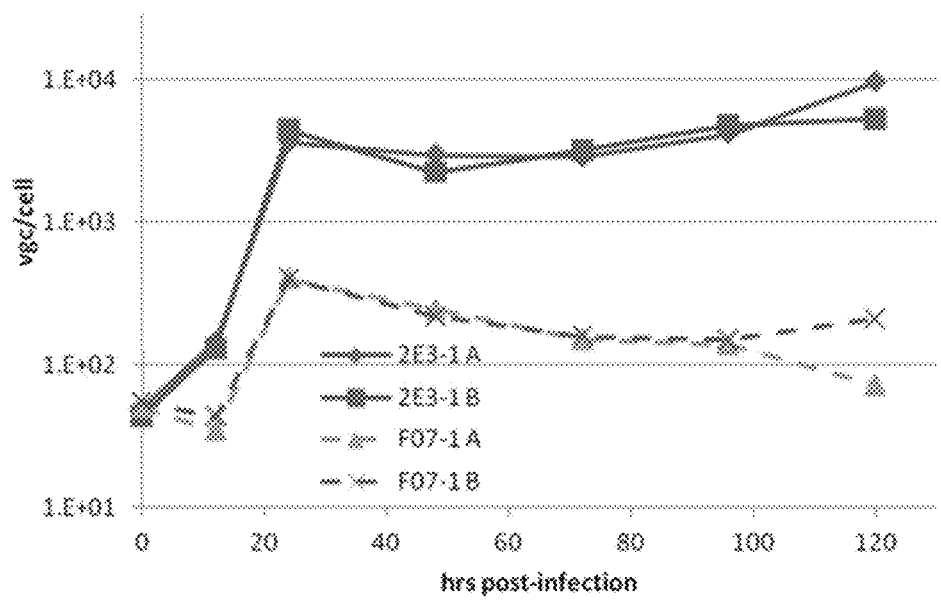
FIG. 4A presents a time course of cell-associated virus after MMV infection. Plotted is MVM virus genome copy (vgc) per cell (based on the assumption that each infected cell can produce4 $2 \times 10^4$ vgc) as detected via qPCR over the course of 120 hours for wild-type (2E3) (solid lines) and COSMC KO clone F07 (broken lines) cells in the presence of MVM virus at MOI of 1.
Figure 4B:
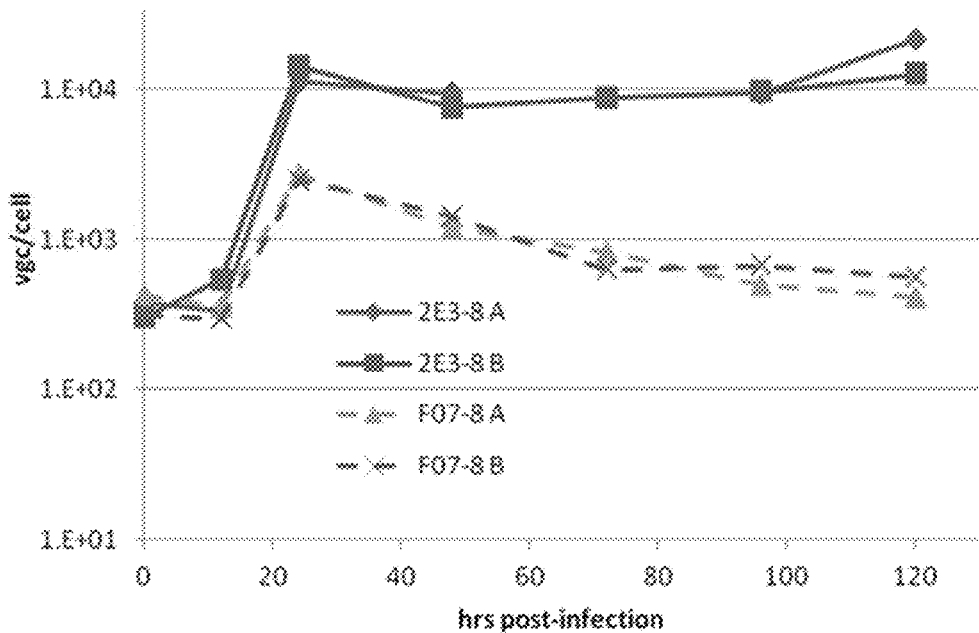
FIG. 4B presents a time course of cell-associated virus after MMV infection. Plotted is MVM virus genome copy (vgc) per cell (based on the assumption that each infected cell can produce4 $2 \times 10^4$ vgc) as detected via qPCR over the course of 120 hours for wild-type (2E3) (solid lines) and COSMC KO clone F07 (broken lines) cells in the presence of MVM virus at MOI of 8.

Cell viability is presented in FIG. 3A, 3B. At 120 hours post infection, cell viability was reduced to about 50% in wild-type cells (i.e., 2E3) (see panel A), whereas in COSMC clone F07 at least 93% of the cells were viable at 120 hours post infection (see panel B). FIG. 4A, 4B shows the time course of cell-associated virus (virus genome copy (vgc) per cell) after MMV infection in wild-type (2E3) and COSMC clone F07 at a MOI of 1 (see panel A) or MOI of 8 (see panel B) (the calculation was based on the assumption that each infected cell can produce $2\times10^4$ vgc). The fraction of infected cells under each condition are presented below.

TABLE 3

Percent of infected cells

| MOI | Cell Type | Replicate | 0 hr | 24 hr | 48 hr | 72 hr | 96 hr | 120 hr |
|---|---|---|---|---|---|---|---|---|
| | | | | | % cells | | | |
| 1 | 2E3 | A | 44 | 21 | 28 | 36 | 24 | 55 |
| | | B | 41 | 27 | 26 | 30 | 32 | 14 |
| | F07 | A | 5 | 2.1 | 1.7 | 1.6 | 0.5 | 1.9 |
| | | B | 6 | 2.2 | 2.0 | 1.4 | 0.7 | 2.5 |
| 8 | 2E3 | A | 115 | 70 | 91 | 42 | 65 | 118 |
| | | B | 105 | 85 | 113 | 55 | 60 | 90 |

TABLE 3-continued

Percent of infected cells

| MOI | Cell Type | Replicate | 0 hr | 24 hr | 48 hr | 72 hr | 96 hr | 120 hr |
|---|---|---|---|---|---|---|---|---|
| | | | | | % cells | | | |
| | F07 | A | 32 | 14 | 12 | 6.9 | 1.1 | 5.5 |
| | | B | 27 | 14 | 11 | 3.4 | 4.8 | 7.5 |

Figure 5A:
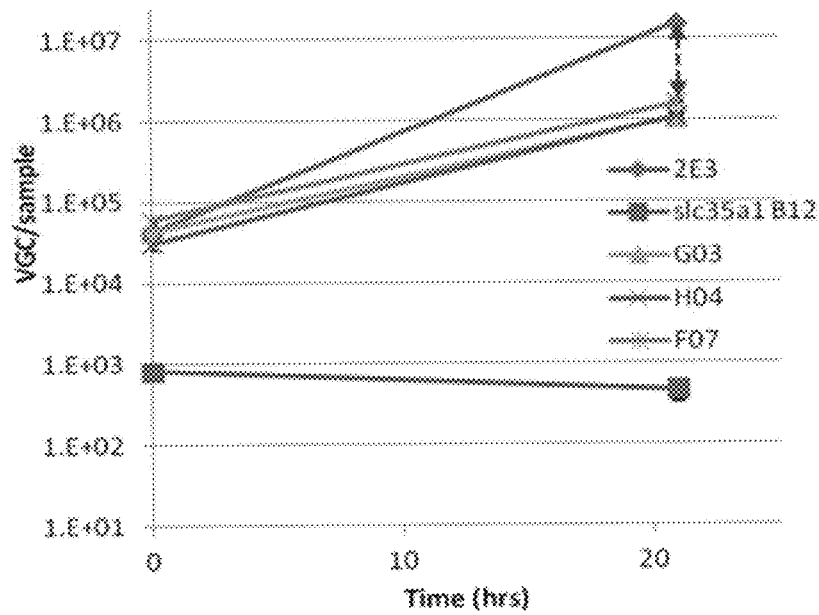
FIG. 5A shows a time course of MMV replication in the indicated cell lines. Plotted is the vgc/sample at 0 and 21 hours after infection with MVM virus at MOI of 0.3.
Figure 5B:
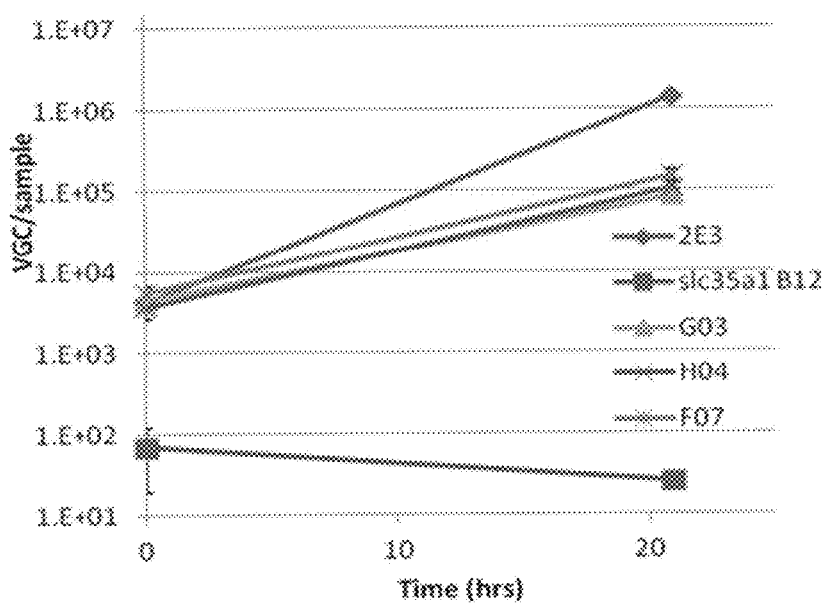
FIG. 5B shows a time course of MMV replication in the indicated cell lines. Plotted is the vgc/sample at 0 and 21 hours after infection with MVM virus at MOI of 0.03.

Wild-type (i.e., 2E3), COSMC KO clones F07, G03, & H04, and Slc35A1 KO clone B12 cells were infected at time −3 hours with MMVp at a MOI of either 0.3 or 0.03. At time 0 hour, the cells were washed three times with growth media and then incubated for 21 hours (i.e., a single replication cycle). Viral replication was assayed by determining cell-associated virus at 0 and 21 hours. As shown in FIG. 5A, 5B, viral replication was reduced in the COSMC KO cell lines and eliminated in the Slc35A1 KO cell line.

Example 5: Resistance of COSMC KO and Slc35A1 KO Cell Lines to Reovirus-3

Figure 6:
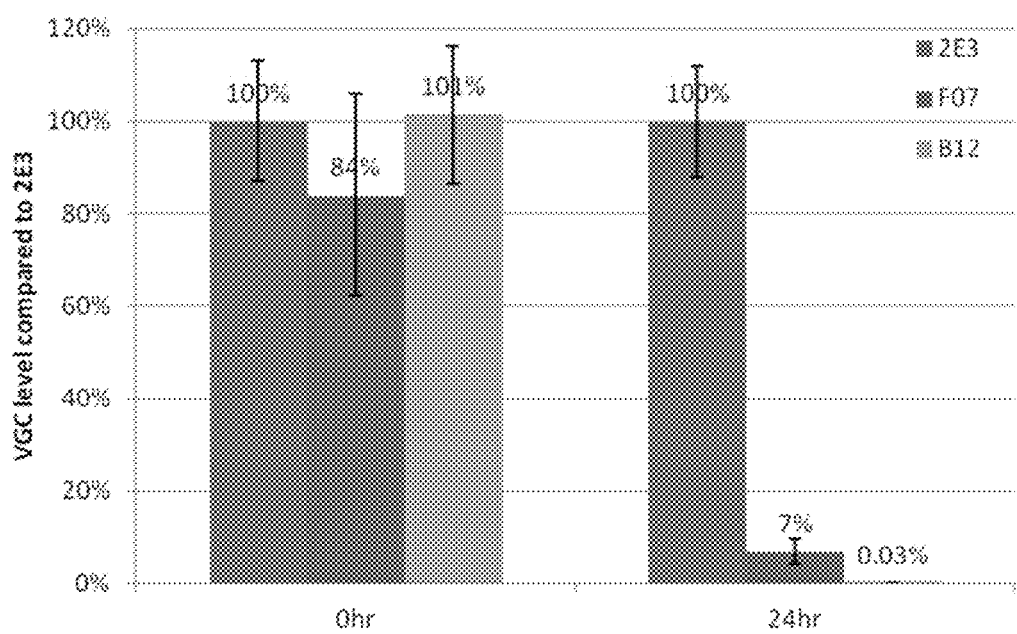
FIG. 6 presents a time course of Reovirus-3 replication in the indicated cell lines. Plotted is the vgc/sample relative to wild-type cells (2E3) at 0 and 24 hours after infection with Reo-3 virus.

Wild-type (i.e., 2E3), COSMC KO clone F07, and Slc35A1 KO clone B12 cells were infected at time −3 hours with reovirus-3 at two dilutions ($TCID_{50}$=5.6E+07 and 5.6E+06). At time 0 hour, the cells were washed three times and then incubated for 24 hours (i.e., a single replication cycle). Viral replication was assayed by determining cell-associated virus at 0 and 24 hours. The levels of cell-associated virus were drastically reduced at 24 hours in the COSMC KO clone and nearly eliminated in the Slc35A1 KO clone (see FIG. 6).

Example 6: Growth Assays of COSMC KO and Slc35A1 KO Cell Lines

Figure 7A:
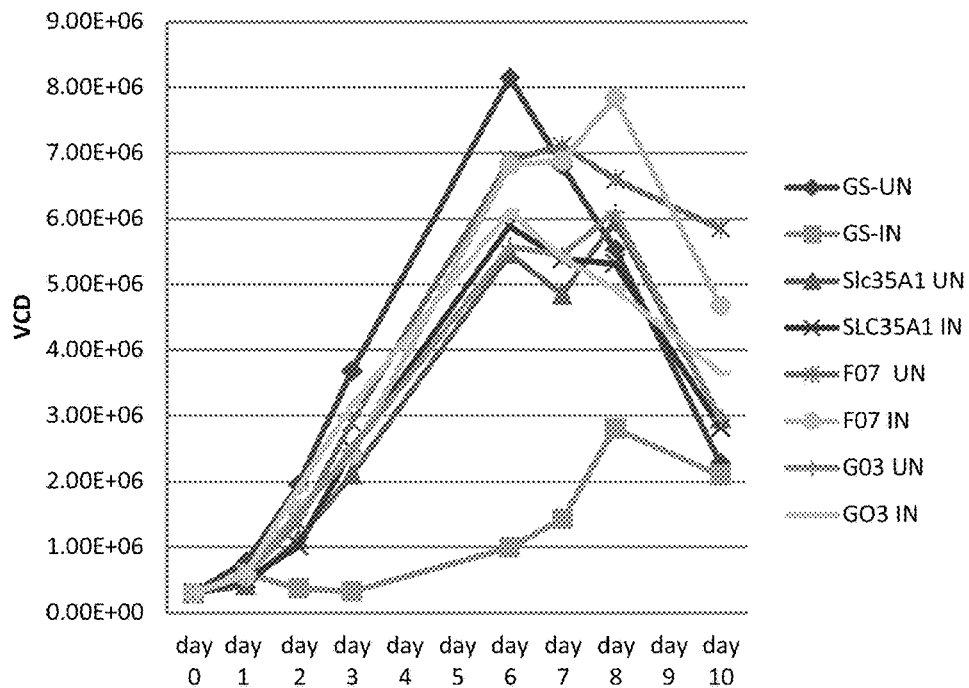
FIG. 7A presents growth assays for cells grown in the absence (UN) or presence (IN) of MVM virus. Plotted is the viable cell density (VCD) for wild-type (GS), Slc35A1 KO, COSMC KO clone F07, and COSMC KO clone G03 over 10 days.

Wild-type (i.e., CHOZN GS−/−), COSMC KO clones F07 & G03, and Slc35A1 KO clone B12 cells were grown in the absence or presence of MVMp virus (at a MOI of 0.1) for 8 to 10 days. Cell growth was monitored by measuring viable cell density (via trypan blue staining) at days 0, 1, 2, 3, 6, 7, 8, and 10. As shown in FIG. 7A, the various KO cells had similar growth profiles in the presence or absence of virus, indicating resistance to viral injection. In contrast, the wild-type cells showed classic infectivity, impaired growth, and low cell viabilities when compared to uninfected cultures.

Figure 7B:
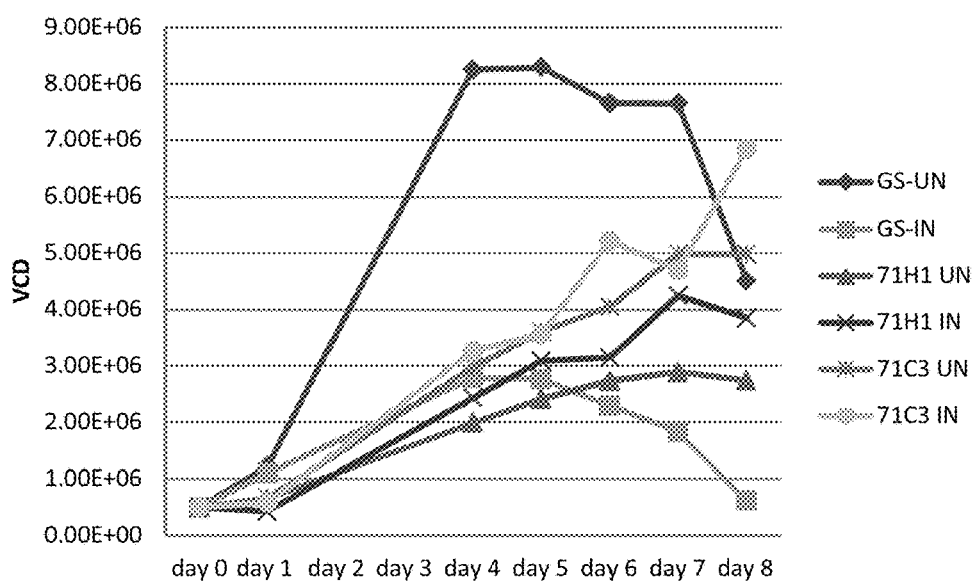
FIG. 7B presents growth assays for cells grown in the absence (UN) or presence (IN) of MVM virus. Plotted is the VCD for wild-type (GS), IgG producing clones 71H1 and 71C3 derived from COSMC KO clone F07 over 8 days.

Cell growth of wild-type and IgG producing clones of COSMC KO clone F07 (i.e., 71H1 and 71C3) was monitored in the absence or presence of virus essentially as detailed above. As shown FIG. 7B, the IgG producing KO cell lines also showed significant resistance to viral infection. Infected cultures grew at similar rates and to a peak cell density as uninfected cultures. These data indicate that secreting a cell surface IgG has no discernable impact on the degree of viral resistance exhibited by the COSMC KO parent. Although both IgG producing cell lines grew at slower rates as compared to wild-type cells, both IgG producers showed resistance to viral infection (i.e. no difference when compared to uninfected cultures).

Example 7: Generation of St3Gal4 KO Cell Line and Cell Growth Assays

St3Gal4 KO cells were generated essentially as described above in example 1 using ZFNs designed to target 5'-GGCAGCCTCCAGTGTCGTCgttgtgTTGTG-GTGGGGAATGGGC (SEQ ID NO: 14) in the CHO St3Gal4 gene. A Cel-1 nuclease assay confirmed the presence of three cleavage fragments (i.e., 344 bp, 210 bp, and 135 bp) in the ZFN transfected cells. Four single cell clones was isolated and sequencing revealed the following mutations. St3Gal4 KO cells have reduced levels of 2-3 linked sialic acid structures.

| Clone | Allele 1 genotype | Allele 2 genotype |
|---|---|---|
| St3Gal4 1B08 | 4 bp insertion | 5 bp deletion |
| St3Gal4 7D10 | 2 bp deletion | 8 bp deletion |
| St3Gal4 1B10 | 5 bp deletion | 11 bp deletion |
| St3Gal4 1H11 | 3 bp insertion | 11 bp deletion |

Figure 8:
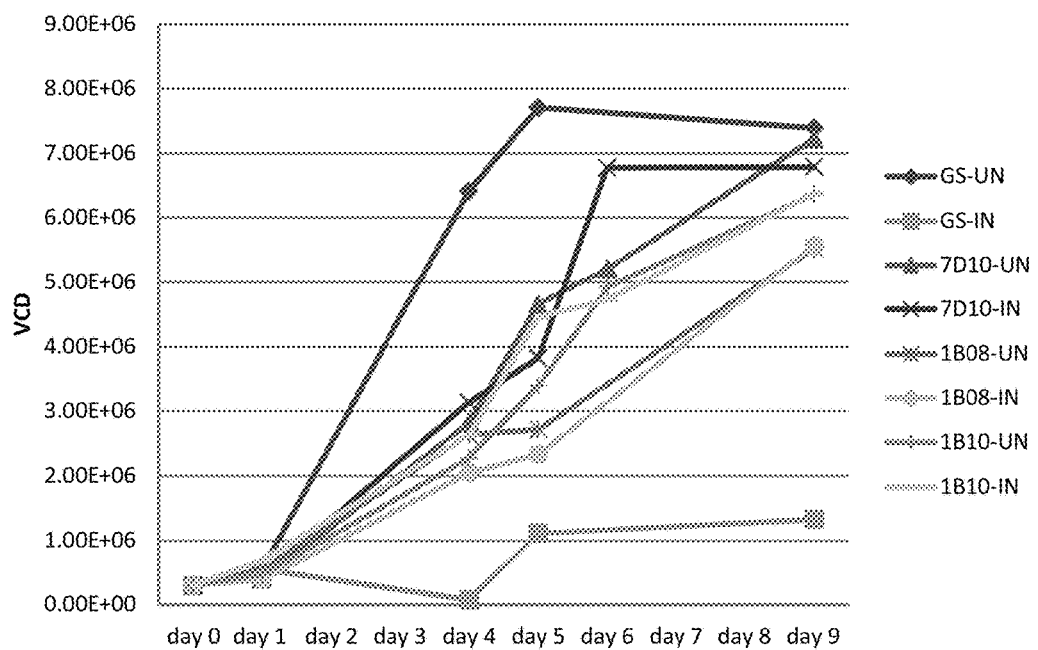
FIG. 8 presents growth assays for cells grown in the absence (UN) or presence (IN) of MVM virus. Plotted is the VCD for wild-type (GS), St3Gal4 KO clone 7D10, St3Gal4 KO clone 1B08, and St3Gal4 KO clone 1B10 over 9 days.

St3Gal4 KO (i.e., clones 7D10, 1B8, and 1B10) and wild-type cells were grown in the absence or presence of MVMp virus at a MOI of 0.1 and cell growth was monitored for 9 days. St3Gal4 KO cells also showed significant resistance to viral infection as show in FIG. 8. Infected KO cultures grew at similar rate and to a peak cell density as the uninfected KO cultures. These studies revealed that disruption of the specific 2-3 linked sialic acid structure on the cell surface, also appears to drastically reduced MVM entry into such cells.

Example 8: Generation of St3Gal4 and St3Gal6 Double KO Cell Line

St3Gal4 KO (i.e., clones 7D10, 1B8, and 1B10) cell lines were used as starting cells to generate cell lines that were also contained a knocked out St3Gal6 gene. ZFNs were designed to target 5'-CGGTACCTCTGATTTTGCTttgc-cCTATGGGACAAGGCC-3' (SEQ ID NO: 15) and gene editing was performed essentially as described in Example 1. A Cel-1 nuclease assay confirmed the presence of three cleavage fragments (i.e., 308 bp, 171 bp, and 137 bp) in the ZFN transfected cells. Six single cell clones was isolated and sequencing revealed the following mutations.

| St3Gal6 clone | Genotype | St3Gal4 cone derivative |
|---|---|---|
| 1E8 | Two different 8 bp deletions + 1 bp substitution | 7D10 |
| 1H8 | 8 bp deletion + 1 bp substitution | 7D10 |
| 2D12 | 4 bp insertion + 2 bp deletion | 1B08 |
| 4F7 | Two different 2 bp deletions | 1B08 |
| 2F11 | 8 bp deletion + 1 bp substitution and 13 bp deletion | 7D10 |
| 3C1 | 8 bp deletion + 1 bp substitution and 8 bp deletion | 7D10 |

Example 9: Generation of C1GalT1 KO Cell Lines

The C1GalT1 gene was knocked out in CHOK1 (GS−/−) cells using ZFNs designed to target 5'-ACCCTCATGCTA-GACatttaGATGATAACGAACCCAGTC-3' (SEQ ID NO: 16) essentially as described in Example 1. A Cel-1 nuclease assay confirmed the presence of two cleavage fragments (i.e., 223 bp and 148 bp) in the ZFN transfected cells. Seven single cell clones was isolated and sequencing revealed the following mutations.

| C1GalT1 Clone | Allele 1 genotype | Allele 2 genotype |
|---|---|---|
| 2A8 | 8 bp deletion | 8 bp deletion |
| 2A11 | 5 bp deletion | 90 bp insertion |
| 2C12 | 8 bp deletion | None detected |
| 2G12 | 5 bp deletion | None detected |
| 3D12 | 8 bp deletion | None detected |
| 3E6 | 1 bp deletion | 2 bp deletion and 97 bp insertion |
| 3F2 | 5 bp deletion | 5 bp deletion and 31 bp insertion |

Staining with biotinylated MALII and Alexa Fluor 647-labeled streptavidin revealed significantly reduced staining in C1GalT1 KO clone 2C12 as compared to the parental cell line.

Example 10: Generation of St6Gal1 Overexpressing Cell Lines

Since it is hypothesized that MVM virus does not bind to alpha-2,6 linked sialic acids, CHO cell lines that overexpress St6Gal1 were generated. The coding sequence of Chinese hamster St6Gal1 was obtained from GenBank (AB492855) and chogenome.org AQ2 (AFTD01061789 and AFTD01061790). The open reading frame was commercially synthesized with a Kozak sequence (5'-GCCGCCAC-CAatg-3'; SEQ ID NO: 18) added to the 5'-untranslated region (UTR). The synthesized fragment was cloned into the expression vector pJ602 (DNA2.0; Menlo Park, Calif.). The CHO (GS−/−) host cell line and an IgG-expressing CHO cell line were transfected (via electroporation) with this construct. Single cell clones were isolated using a FACSAria™ III cell sorter. For this, cells were stained with FITC-conjugated *Sambucus Nigra* lectin (FITC-SNA), which binds α-2,6 linked sialic acid, and cells with the top 5% fluorescence were plated at 1 cell/well and cultured. Single cell clones were subjected to two-color FACS analysis on a MACSQuantVR Analyzer (Miltenyi Biotec, San Diego, Calif.) after staining with biotinylated MALII, which binds α-2,3 linked sialic acid, and Alexa Fluor 647-labeled streptavidin. The St6Gal1 overexpressing single cell clones had increased ratios of FITC to AlexaFluor as compared to non-transfected parental cell lines.

IgG was isolated from two St6Gal1 overexpressing clones (i.e., clone 31 and clone 32) and the parental cell clone. IgG or total cellular protein extracts were reduced and carboxyamidomethylated according to standard procedures prior to trypsinization at 37° C. overnight (12-16 h). Trypsin was deactivated by heating at 100° C. for 5 min. Purification of fragments was carried out with a C18 SPE cartridge (Waters, 300 mg packing). After a wash with 5% acetic acid (AcOH), the peptides/glycopeptides were eluted sequentially in 20% isopropanol/5% AcOH, 40% isopropanol/5% AcOH, and 100% isopropanol. The eluent was dried down, reconstituted in phosphate buffer containing PNGase F, and incubated at 37° C. overnight. The released glycans were purified using a C18 cartridge, permethylated and diluted into 1 mM lithium carbonate/50% MeOH and infused directly into an LTQ Orbitrap Discovery Mass Spectrometer (Thermo Scientific) at a flow rate of 0.5 mL/min for nanospray ionization. A full Fourier transform mass spectrometry (FTMS) spectrum was obtained at a 30,000 resolution for each sample to determine which glycans contained sialic acids. The sialic acid linkage of the sialylated glycans was determined by MSn analysis. Each sample was subjected to multiple ion selection and fragmentation steps within the ion trap to break down a complex-type glycan down to a single galactose and then, the fragmentation pattern was observed.

There were striking differences between the N-glycan profiles of the GS (−/−) host-cell line and the two St6Gal1 overexpressing cell lines (i.e., clones 31 and 32). In particular, no sialylated glycans were identified in the host-cell line, due to their low abundance. By contrast, mono-, bi-, tri-, and tetrasialylated N-glycans were identified in both St6Gal1 overexpressing cell lines. In particular, all but one sialylated population in clone 32 was shown to contain both α-2,3- and α-2,6-linkages.

What is claimed is:

1. A genetically modified mammalian cell line which is resistant to infection by minute virus of mouse (MVM), as compared to an unmodified parental cell line, wherein the genetically modified mammalian cell line, comprises a modified chromosomal sequence comprising an inactivated chromosomal sequence encoding St3 beta-galactoside alpha-2,3-sialyltransferase 4 (St3Gal4).

2. The genetically modified mammalian cell line of claim 1, further comprising an inactivated chromosomal sequence encoding mannosyl (alpha-1,3-)-glycoprotein beta-1,2-N-acetylglucosaminyltransferase 1 (Mgat1).

3. The genetically modified mammalian cell line of claim 1, wherein the modified chromosomal sequence is modified using a targeting endonuclease-mediated genome modification technique.

4. The genetically modified mammalian cell line of claim 3, wherein the targeting endonuclease is a zinc finger nuclease.

5. The genetically modified mammalian cell line of claim 1, further comprising at least one nucleic acid encoding a recombinant protein chosen from an antibody, an antibody fragment, a vaccine, a growth factor, a cytokine, a hormone, or a clotting factor.

6. The genetically modified mammalian cell line of claim 1, wherein the cell line is a non-human cell line.

7. The genetically modified mammalian cell line of claim 1, wherein the cell line is a Chinese hamster ovary (CHO) cell line.

8. The genetically modified mammalian cell line of claim 1, further comprising at least one inactivated chromosomal sequence encoding glutamine synthetase.

9. The genetically modified mammalian cell line of claim 1, for use in a biologic production system.

10. A method for reducing the risk of viral contamination of a biologic production system, the method comprising providing for use in the biologic production system the genetically modified mammalian cell line of claim 1.

11. A method for reducing or preventing viral contamination of a recombinant protein product, the method comprising:
   a) obtaining the genetically modified mammalian cell line of claim 1; and
   b) expressing the recombinant protein product in the genetically modified mammalian cell line.

* * * * *